(12) United States Patent
Carpentier et al.

(10) Patent No.: US 6,391,054 B2
(45) Date of Patent: May 21, 2002

(54) EXPANDABLE ANNULOPLASTY RING

(75) Inventors: Alexandre Carpentier; Alain Carpentier, both of Paris (FR)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/785,976

(22) Filed: Feb. 16, 2001

Related U.S. Application Data

(62) Division of application No. 09/124,657, filed on Jul. 29, 1998, now Pat. No. 6,217,610, which is a continuation-in-part of application No. 09/100,451, filed on Jun. 19, 1998, now abandoned, and a continuation-in-part of application No. 08/898,176, filed on Jul. 22, 1997, now abandoned, which is a continuation of application No. 08/898,908, filed on Jul. 22, 1997, now abandoned, said application No. 08/898,908, and application No. 08/898,176, which is a continuation-in-part of application No. 08/757,693, filed on Dec. 3, 1996, now Pat. No. 5,888,240, which is a continuation of application No. 08/283,059, filed on Jul. 29, 1994, now Pat. No. 5,593,435.

(51) Int. Cl.[7] ................................................. A61F 2/06
(52) U.S. Cl. ...................................................... 623/2.37
(58) Field of Search ................................ 623/2.36, 2.37

(56) References Cited

U.S. PATENT DOCUMENTS

| | | | |
|---|---|---|---|
| 4,042,979 A | 8/1977 | Angell | |
| 4,055,861 A | 11/1977 | Carpentier et al. | |
| 4,106,129 A | 8/1978 | Carpentier et al. | |
| 4,164,046 A | * 8/1979 | Cooley ....................... | 623/2.36 |

(List continued on next page.)

FOREIGN PATENT DOCUMENTS

| | | |
|---|---|---|
| DE | 3230858 | 8/1982 |
| EP | 0-338-994 | 10/1989 |
| FR | 2306671 | 4/1975 |
| FR | 2726757 | 11/1994 |
| RU | 197710 | 10/1977 |
| WO | WO 91/17721 | 11/1991 |
| WO | WO9603938 | 2/1996 |
| WO | WO 97/19655 | 6/1997 |

OTHER PUBLICATIONS

Cardiovascular Surgery 1980, Proceedings of the 29th International Congress of The European Society of Cardiovascular Surgery, "Conservative Surgery of the Mitral Valve. Annuloplasty on a new Adjustable Ring"; pp. 29–37; M. Puig Massana, J. M. Calbet, and E. Castells.

The Annals of Thoracic Surgery, "Clinical and Hemodynamic Performance of Totally Flexible Prosthetic Ring for Atrioventricular Valve Reconstruction", Carlos G. Duran, M.D., Ph.D., Jose Luis M. Ubago, M.D.; vol. 22, No. 5, Nov. 1976; pp. 458–463.

*Primary Examiner*—Bruce Snow
(74) *Attorney, Agent, or Firm*—Debra D. Condino; John Christopher James; Guy L. Cumberbatch

(57) ABSTRACT

An expandable annuloplasty ring which may either expand spontaneously, in situ, as the patient grows or be expanded by surgical intervention by balloon dilatation. The distensible annuloplasty ring of the invention may be usable in pediatric patients whose growth, subsequent to surgical implantation of the ring, will necessitate subsequent enlargement of the ring to accommodate growth of the annulus. The ring may include a solid core of non-elastic material which plastically retains its shape upon natural expansion of the annulus, or after surgical expansion. A discontinuity may be positioned along the anterior side of the ring or around the posterior side.

10 Claims, 22 Drawing Sheets

U.S. PATENT DOCUMENTS

| | | |
|---|---|---|
| 4,183,102 A | 1/1980 | Guiset |
| 4,290,151 A | 9/1981 | Massana |
| 4,345,340 A | 8/1982 | Rosen |
| 4,489,446 A | 12/1984 | Reed |
| 4,535,483 A | 8/1985 | Klawitter et al. |
| 4,602,911 A | 7/1986 | Ahmadi et al. |
| 4,917,698 A | 4/1990 | Carpentier et al. |
| 5,061,277 A | 10/1991 | Carpentier et al. |
| 5,064,431 A | 11/1991 | Gilbertson et al. |
| 5,071,431 A | 12/1991 | Sauter et al. |
| 5,104,407 A | 4/1992 | Lam et al. |
| 5,163,953 A | 11/1992 | Vince |
| 5,201,880 A | 4/1993 | Wright et al. |
| 5,258,021 A | 11/1993 | Duran |
| 5,306,296 A | 4/1994 | Wright et al. |
| 5,593,424 A | 1/1997 | Northrup |
| 5,593,435 A | 1/1997 | Carpentier et al. |
| 5,607,471 A | 3/1997 | Seguin et al. |
| 5,628,790 A | 5/1997 | Davidson et al. |
| 5,674,280 A * | 10/1997 | Davidson et al. ............... 623/2 |
| 5,716,397 A | 2/1998 | Myers |
| 5,888,240 A | 3/1999 | Carpentier et al. |
| 6,203,551 B1 * | 3/2001 | Wu ........................... 623/108 |

\* cited by examiner

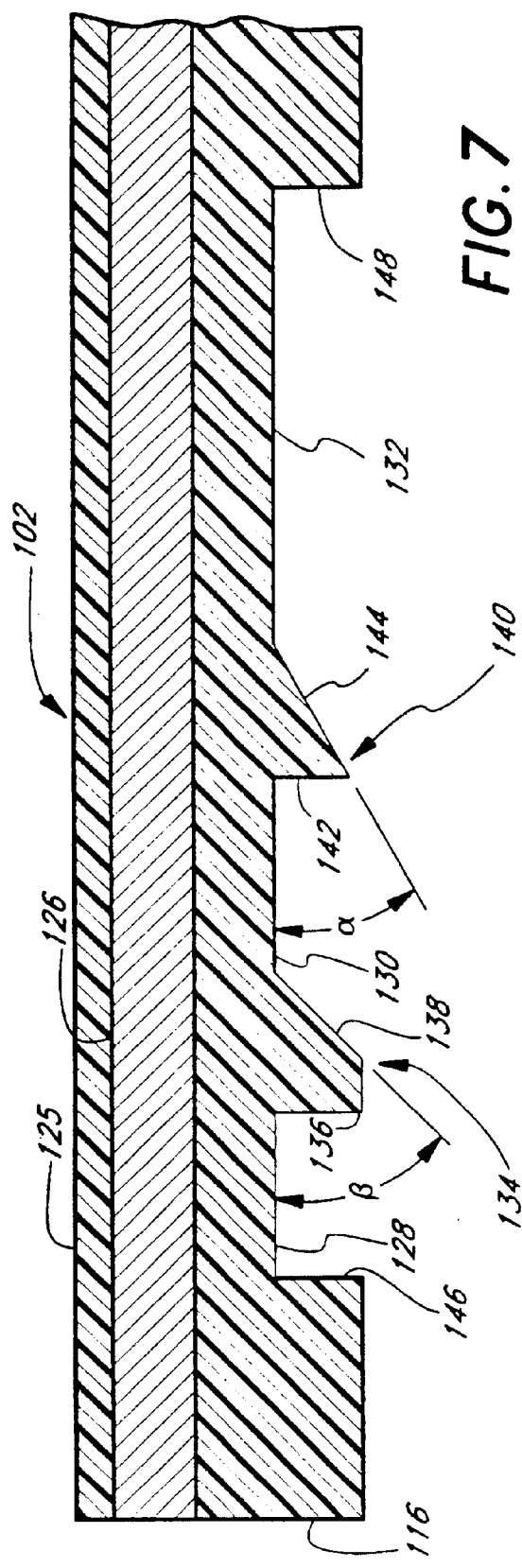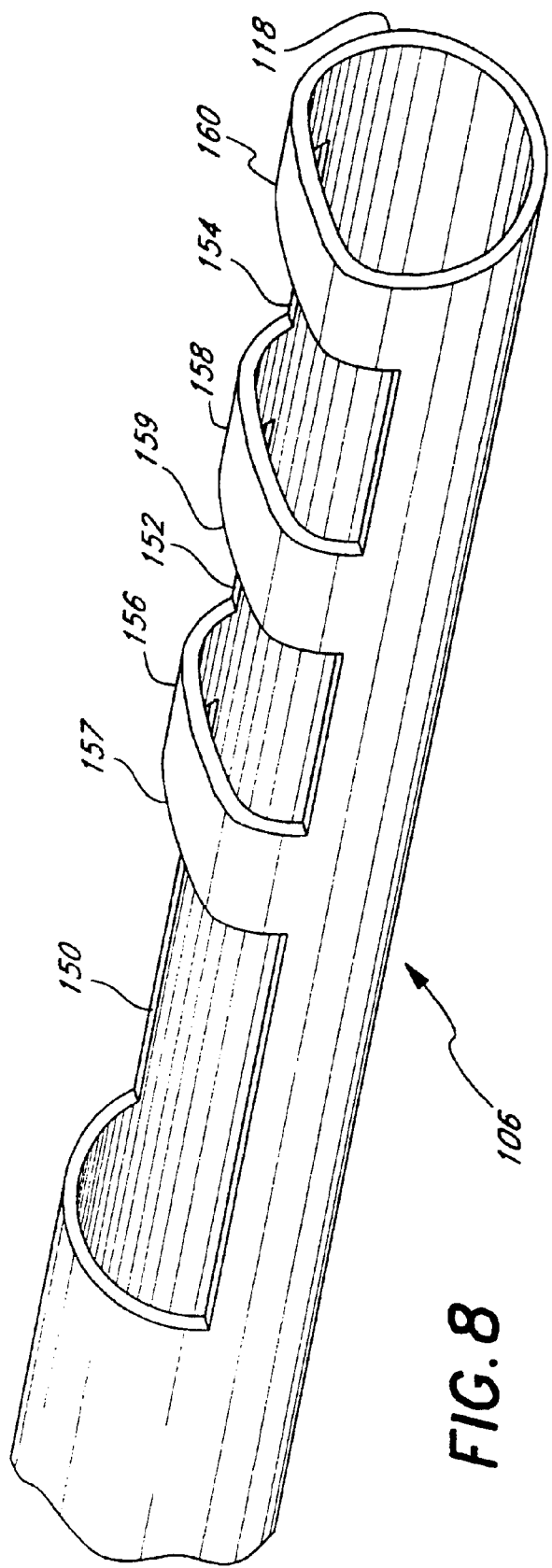

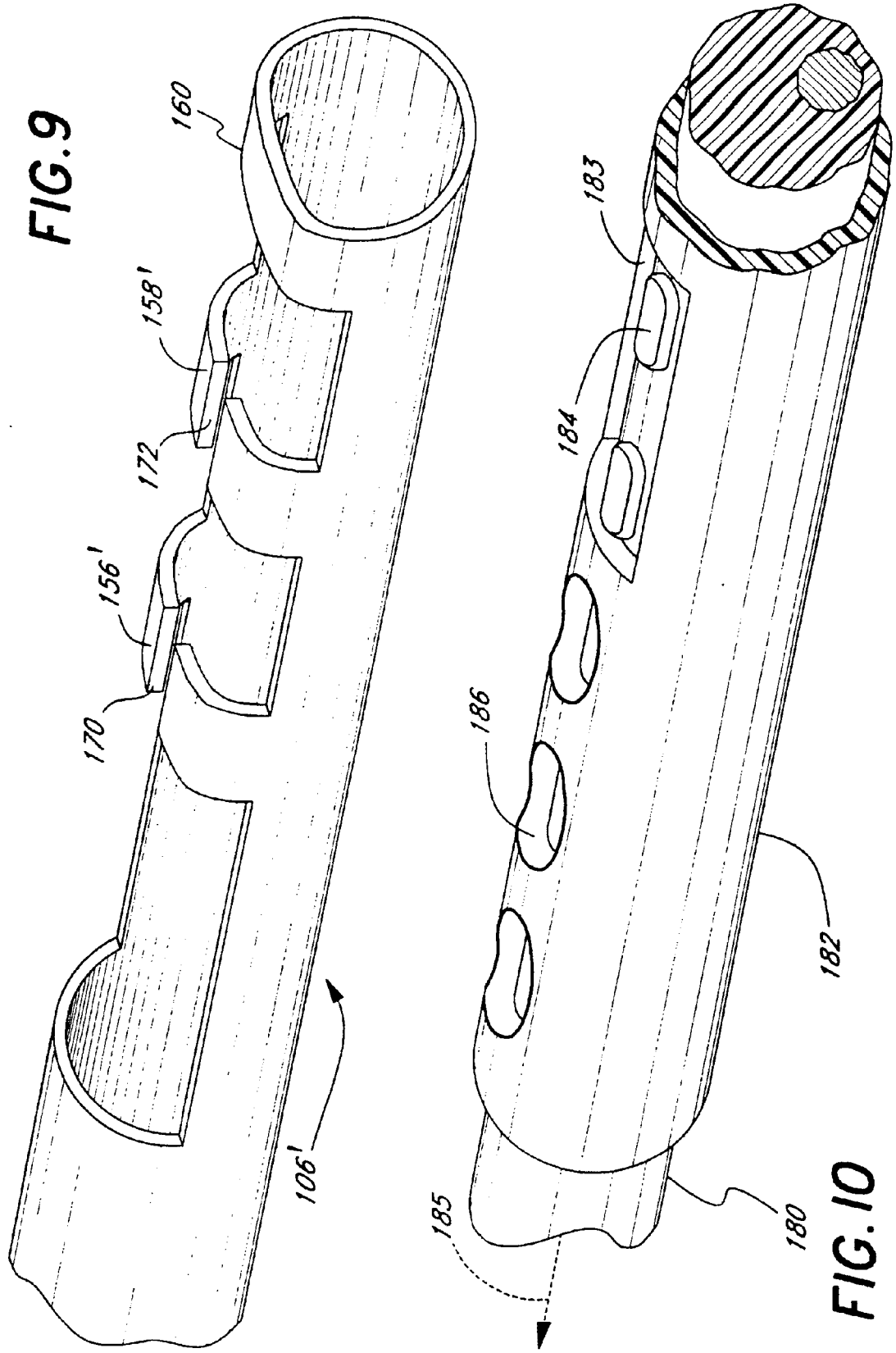

FIG.11
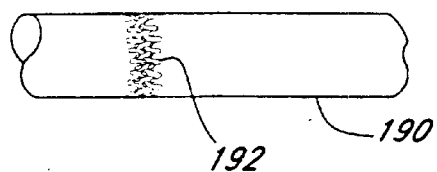
FIG.12
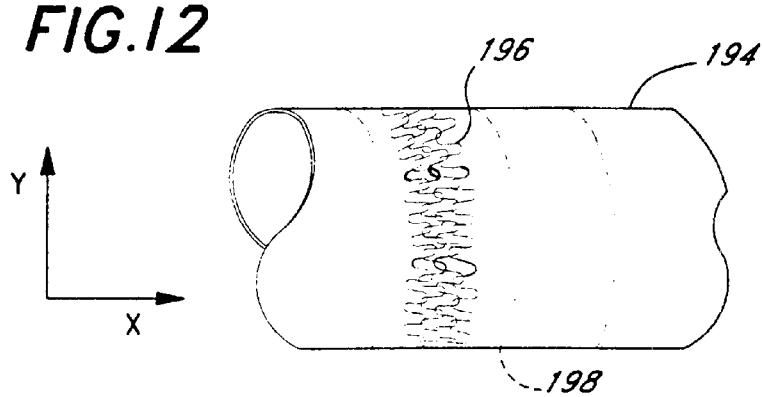
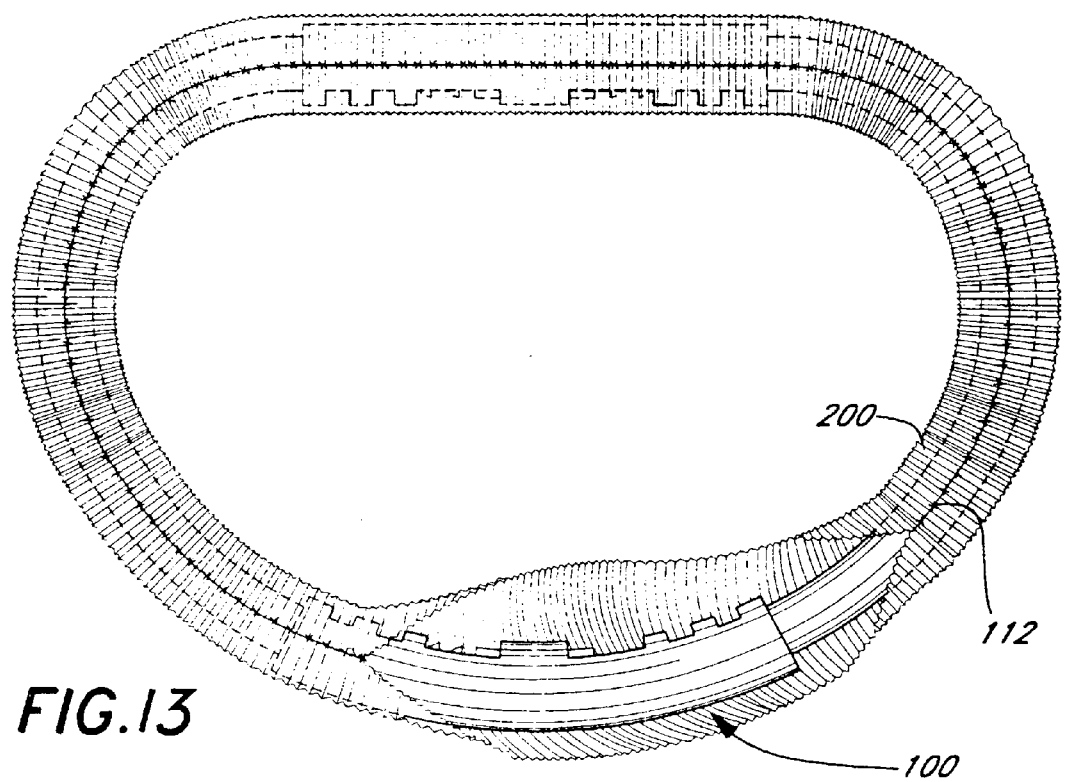
FIG.13

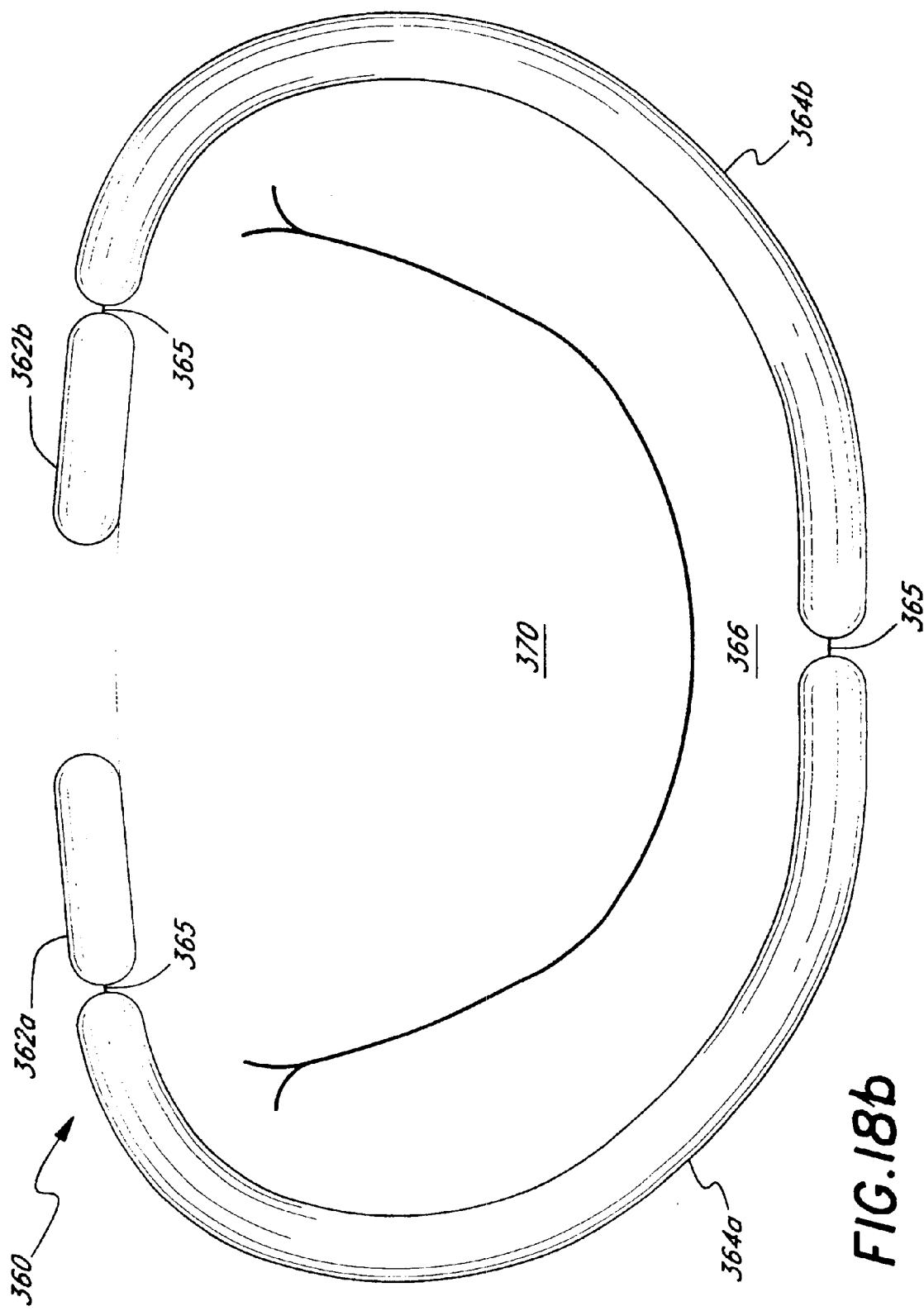

EXPANDABLE ANNULOPLASTY RING

RELATED APPLICATIONS

The present application is a divisional of U.S. Application Ser. No. 09/124,657 and now U.S. Pat. No. 6,217,610, B1, filed Jul. 29, 1998 and issued Apr. 17, 2001, which is a continuation-in-part of U.S. Ser. No. 08/898,176, filed Jul. 22, 1997 and now abandoned, and a continuation-in-part of U.S. Ser. No. 09/100,451, filed Jun. 19, 1998 and now abandoned, which in turn is a continuation of U.S. Ser. No. 08/898,908, filed Jul. 22, 1997 and now abandoned. Both U.S. Ser. No. 08/898,176 and U.S. Ser. No. 08/898,908 are continuations-in-part of Application Ser. No. 08/757,693 and now U.S. Pat. No. 5,888,240, filed Dec. 3, 1996 and issued Mar. 30, 1999, which is a continuation of Application Ser. No. 08/283,059 and now U.S. Pat. No. 5,593,435, filed Jul. 29, 1994 and issued Jan. 14, 1997. The disclosures of these prior applications are hereby incorporated herein by reference.

FIELD OF THE INVENTION

The present invention relates generally to medical devices, and more particularly to an annuloplasty ring useable for surgical correction of certain disorders of the atrioventricular (i.e., mitral and tricuspid) valves of the human heart.

BACKGROUND OF THE INVENTION

In many patients who suffer from disfunction of the mitral and/or tricuspid valves(s) of the heart, surgical repair of the valve (i.e., "valvuloplasty") is a desirable alternative to valve replacement. One specific group of patients who are typically candidates for such surgery is children who suffer from congenital valvular anomaly (CVA) or rheumatic valvular disease (RVD).

Remodeling of the valve annulus (i.e., "annuloplasty") is central to many reconstructive valvuloplasty procedures. In 1968, Dr. Alain Carpentier published studies which demonstrated that such remodeling of the valve annulus might be accomplished by implantation of a prosthetic ring (i.e. "annuloplasty ring") to stabilize the annulus and to correct or prevent valvular insufficiency that may result from defect disfunction of the valve annulus. Annuloplasty rings are typically constructed of a resilient core covered with a fabric sewing ring. Annuloplasty procedures are performed not only to repair damaged or diseased annuli, but also in conjunction with other procedures, such as leaflet repair.

The prior art has included numerous annuloplasty rings, such as those described in U.S. Pat. Nos.: 4,042,979 (Angell), U.S. Pat. No. 4,290,151 (Massana); U.S. Pat. No. 4,489,446 (Reed); U.S. Pat. No. 4,602,911 (Ahmadi et al.); U.S. Pat. No. 5,061,277 (Carpentier et al.); and U.S. Pat. No. 5,201,880 (Wright et al.), as well as International Patent Publication WO 91/17721 and Foreign Patent Publication SU 197710.

One problem associated with the annuloplasty rings of the prior art is that when such annuloplasty rings are implanted into children or adolescents (such as pediatric patients with CVA or RVD) the subsequent growth of the patient may render the annuloplasty ring too small for its intended function, thus abnormally constricting the annulus. The mitral annulus, for example, typically grows from about 16 mm across its longest dimension, to about 34 mm in adults. Follow-up surgery would be necessary to replace the originally implanted annuloplasty ring with a larger ring suitable for the then-current size of the patient. However, the tissue of the heart valve annulus grows into the fabric suture ring by design so that the ring is soon embedded in living tissue, making such replacement surgery problematic. Therefore, reconstructive valvuloplasty surgery on younger patients is often done using just sutures to bolster the annulus, or in conjunction with pieces of woven polyester or other biocompatible material. Such repairs may restore the normal geometry of the annulus, but are unlikely to maintain that geometry without additional structural support, and therefore are associated with less reliable and durable results.

Although some of the annuloplasty rings of the prior art have incorporated means for adjusting the size of the ring at the time of implantation, the inventors are aware of no prior art annuloplasty ring constructed and equipped for post-implantation size adjustment, in situ, to accommodate changes in annular size due to growth of the patient.

SUMMARY OF THE INVENTION

The present invention provides an expandable annuloplasty ring for implantation in a heart valve annulus. Desirably, the ring is adapted to expand upon natural growth of the patient's annulus, or upon application of a dilatation force surgically applied. A fabric covering is preferably radially expandable.

In accordance with the invention, the annuloplasty ring may be formed of a non-elastic polymer or other distensible material, such as polyacetyl, which will remain distended after the application of natural growth forces or outward dilatory pressure has been terminated. Desirably, the non-elastic ring includes a discontinuity positioned in a more stable area of lower growth such as in the straight side of a D-shaped ring that is positioned on the anterior side of the mitral valve annulus.

In a preferred method of repairing a heart valve annulus, an adjustable annuloplasty ring is implanted in the annulus. The size of the implanted annuloplasty ring may be adjusted by inserting a dilation apparatus into the valve in which the annuloplasty ring is implanted and distending the annuloplasty ring to a larger annular size. The step of adjusting may include advancing a catheter transluminally through the vasculature to a point where the distal end of the catheter is positioned adjacent the valve wherein the annuloplasty ring is implanted, and subsequently advancing said dilation apparatus through said catheter and into its desired position within the valve for subsequent dilation of the annuloplasty ring. Alternatively, the ring may be capable of expanding upon growth of the annulus. Expansion of the implanted self-expanding annuloplasty ring may still be assisted by inserting a dilation apparatus into the valve in which the annuloplasty ring is implanted and distending the annuloplasty ring to a larger annular size.

In accordance with a further aspect of the present invention, a distensible annuloplasty ring is provided which may expand, in situ, spontaneously from the forces exerted by growth of the heart, or by way of transvascularly and/or transseptally positionable valve expansion apparatus. When dilatory or outward pressure is exerted against the ring, as may be accomplished spontaneously from the forces exerted by growth of the heart, or by way of a radially expandable member (e.g., a balloon or expandable wire cage) introduced within the annulus of the remodeled valve, such pressure will expand the ring to a larger annular size.

Still further in accordance with the invention, there is provided a method for performing remodeling annuloplasty of an atrioventricular valve, with, if necessary, a subsequent transluminal and/or transeptal procedure for enlargement of the annuloplasty ring to accommodate growth of the patient.

Further objects and advantages of the invention will become apparent to those skilled in the art, upon reading of the following Detailed Description of the Preferred Embodiments and consideration of the accompanying drawings.

BRIEF DESCRIPTION OF THE DRAWINGS

FIG. 3a is an enlarged cut away plan view of a portion of the annuloplasty ring of FIG. 3;

FIG. 7 is an enlarged cross-sectional view of one end of a ring segment forming a portion of the annuloplasty ring of FIG. 5 taken along line 7—7 of FIG. 6;

FIG. 8 is a perspective view of an end of a coupling tube forming a portion of the annuloplasty ring of FIG. 5;

FIG. 9 is a perspective view of an end of an alternative coupling tube for the annuloplasty ring of FIG. 5;

FIG. 10 is a perspective view of an end of a ring segment within a coupling tube of an alternative adjustable annuloplasty ring of the present invention;

FIG. 11 is a plan view of a portion of a fabric tube conventionally used in covering annuloplasty rings;

FIG. 12 is a plan view of a portion of an enlarged tube of fabric material having a similar weave as the smaller tube shown in FIG. 11, and used for the annuloplasty rings of the present invention;

FIG. 13 is a plan view of the annuloplasty ring of FIG. 5 showing a section of the enlarged fabric tube of FIG. 12 surrounding the inner ring structure just prior to a final step in forming the ring;

FIG. 18b is a plan view of the annuloplasty ring of FIG. 18a after a period of time after implantation, and subsequent growth of the mitral valve annulus;

DESCRIPTION OF THE PREFERRED EMBODIMENTS

Figure 1:
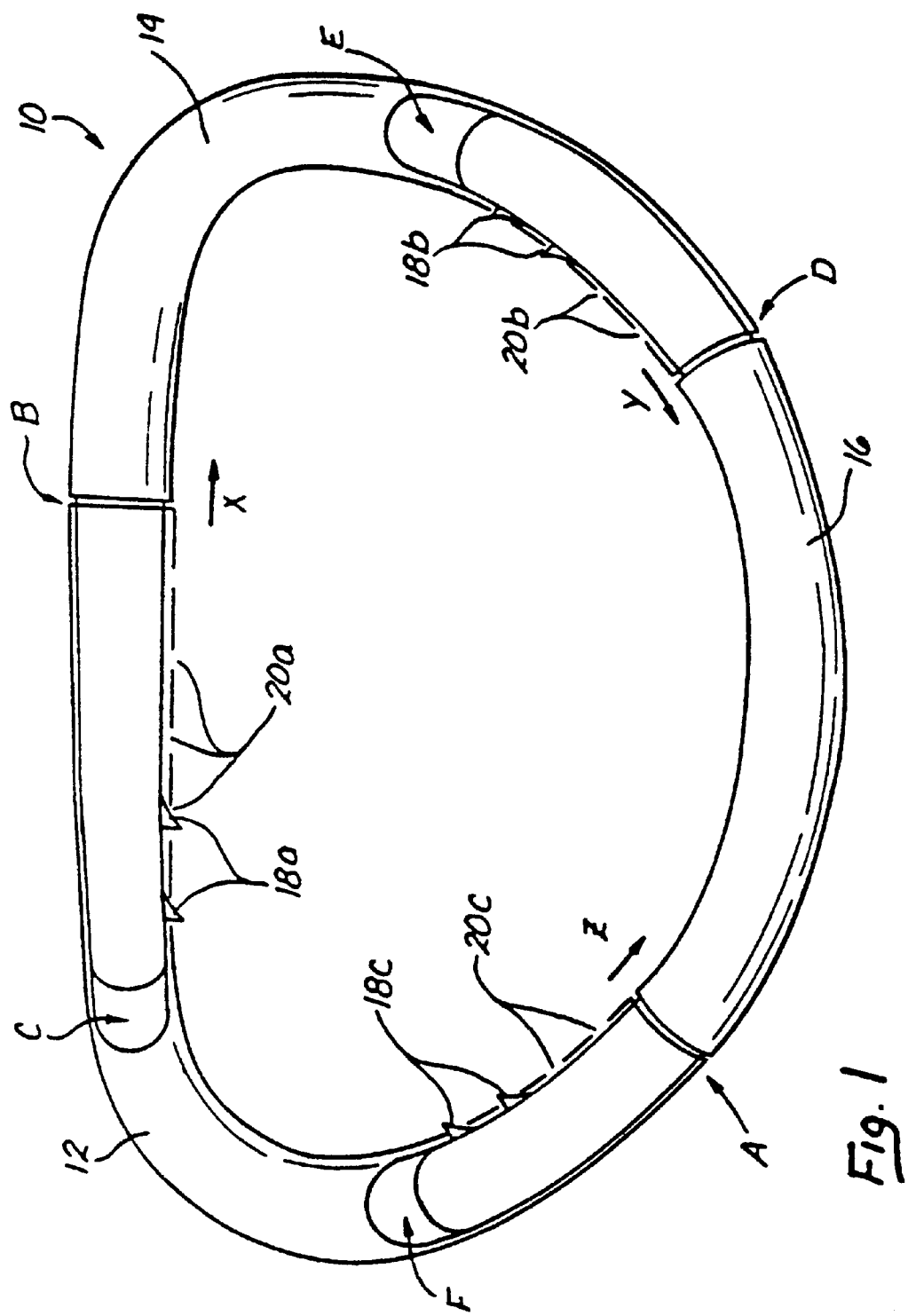
FIG. 1 is a plan view of a first embodiment of the adjustable annuloplasty ring of the present invention.

The following detailed description and the accompanying drawings are intended to describe and show certain presently preferred embodiments of the invention only, and are not intended to limit the spirit or scope of the invention in any way.

The present invention provides annuloplasty rings which correct various valvular deficiencies stemming from a number of conditions such as congenital valvular anomaly (CVA) or rheumatic valvular disease (RVD), are expandable after implantation, and provide support over extended periods. In addition, the rings are used in conjunction with other procedures, such as leaflet repairs. Some annuloplasty rings presently available can be adjusted during the step of implantation to better fit the ring to the particular annulus size, but the nominal ring size then remains constant for its implanted life. The post-implantation expandability of the present ring prolongs its implanted life and eliminates later surgical removal and replacement operations in some instances. The expandable annuloplasty rings of the present invention are primarily intended for implantation in pediatric or younger patients whose annuli are not fully developed. Depending on the final adult annulus size, the present ring could provide a permanent annulus support for the life of the patient. Because of the expandable nature of the rings, a resection operation may not be necessary. Larger patients may have to undergo a second reconstructive valvuloplasty operation, however, to ensure optimum ring performance.

The adjustability of the ring can be accomplished in two primary ways: surgically or naturally. In a surgical adjustment method, a balloon dilatation catheter or other such device is positioned within the ring annulus and expanded. This dilates the ring and increments its size. Though the surgical expansion is beneficial for some patients, one primary advantage of the present ring over the prior art is the capability of the ring to self-expand upon natural growth of the valve annulus. This natural expansion obviates further surgery to adjust the ring size and is thus preferable over the surgical expansion method.

In one embodiment, upon balloon dilatation or as the patient grows, the ring incrementally expands and "locks" into gradually larger sizes. The particular construction of the ring allows incremental expansion and prevents contraction. The present invention also discloses a number of annuloplasty rings that expand upon growth of the natural annulus without structure for maintaining (or locking) the expanded shape. The rings are intended to conform to the shape of the natural annulus, and maintain or approximate that shape as the annulus grows.

Although the various embodiments of the expandable annuloplasty ring of the present invention are designed to correct deficiencies in the mitral valve annulus, those of skill in the art will recognize that other shapes of rings for correcting other of the heart's annuli (such as the tricuspid annulus) may be constructed in accordance with the teachings of the present invention.

Closed, Ratcheted, Segmented Annuloplasty Rings

Figure 2:
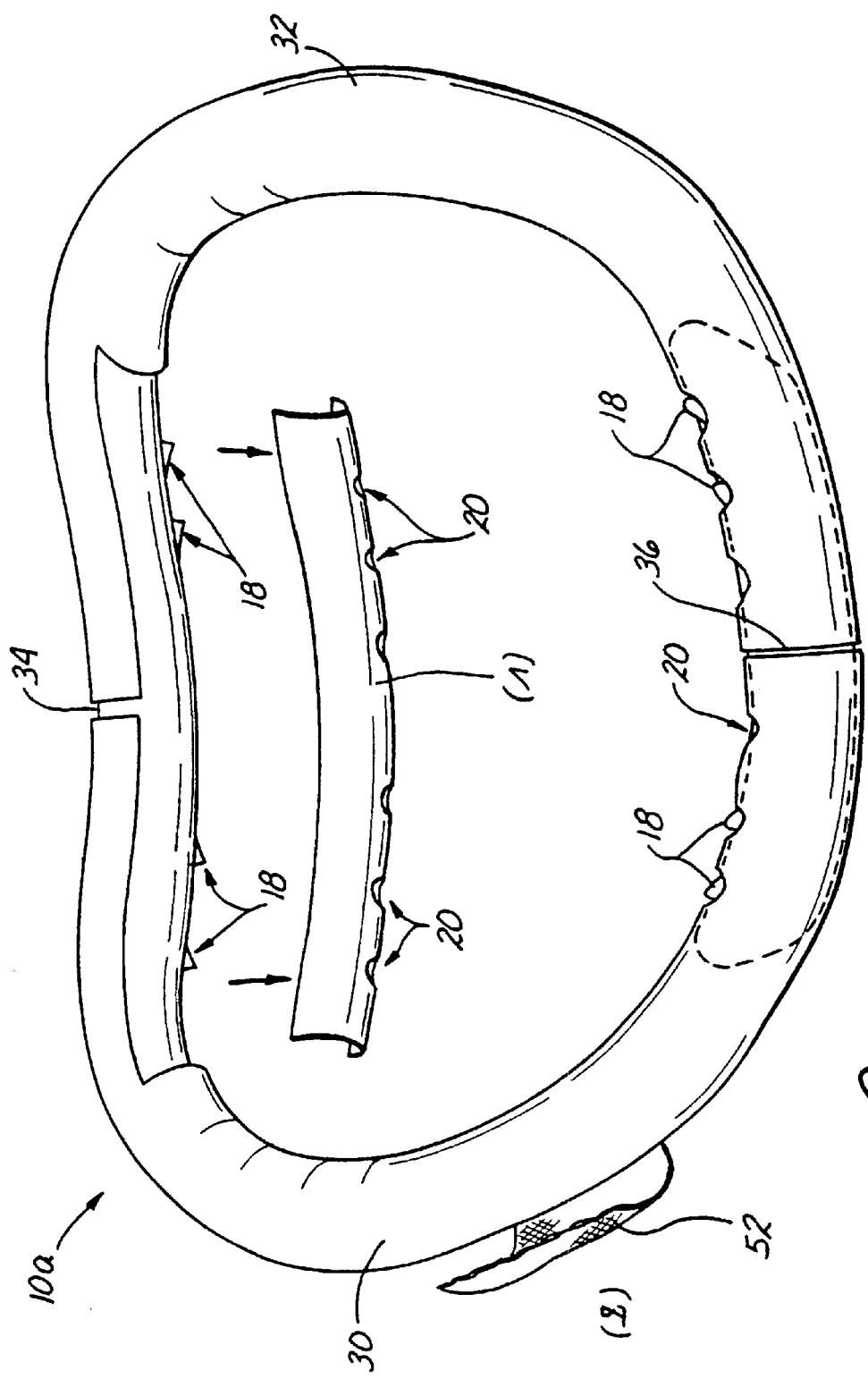
FIG. 2 is a partial cut-away plan view of a second embodiment of the adjustable ring of the present invention.
Figure 3:
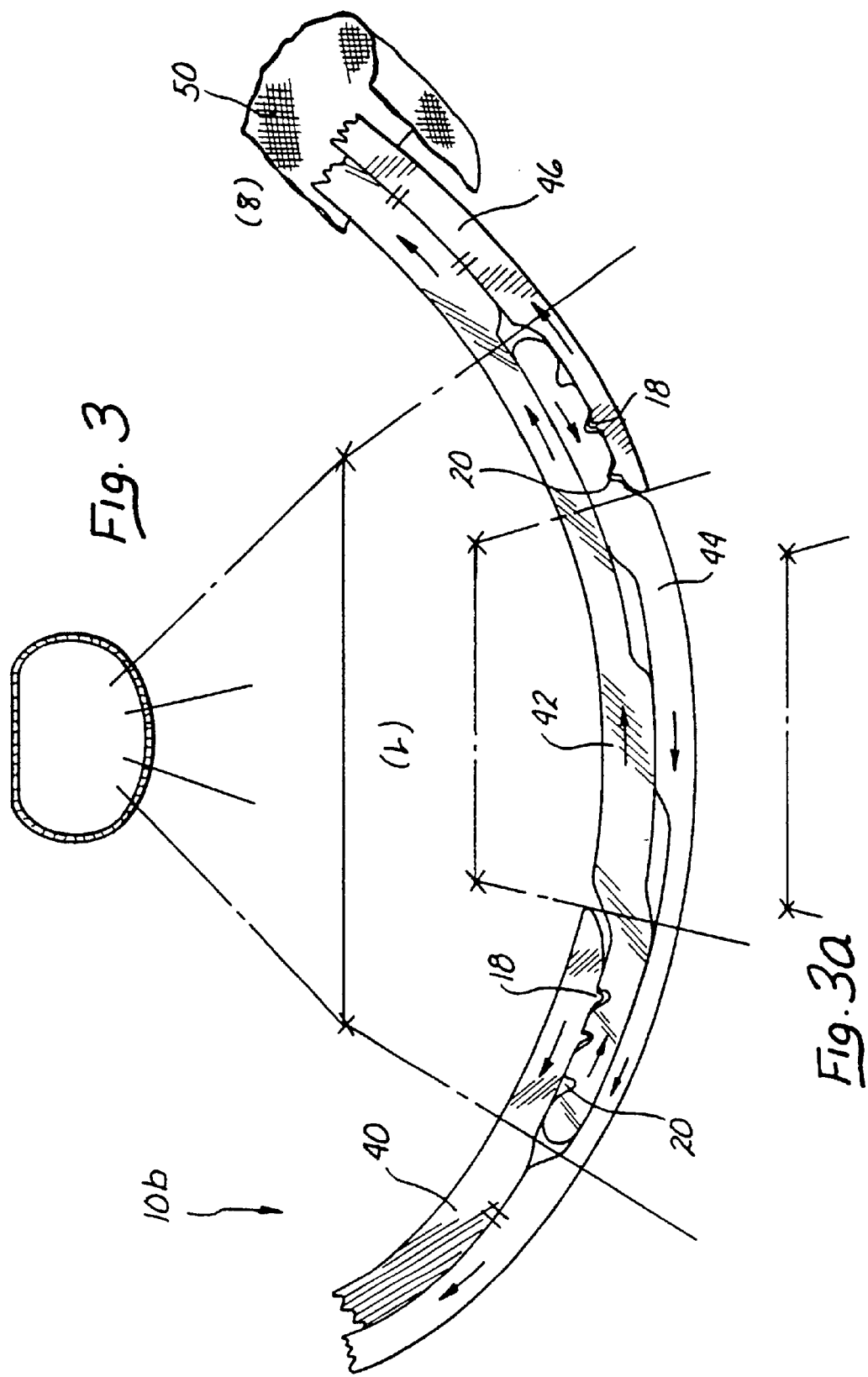
FIG. 3 is a reduced plan view of a third embodiment of the adjustable annuloplasty ring of the present invention.

With reference to the drawings, FIGS. 1–3 show alternative ways of constructing the adjustable ring member 10, 10a and 10b of the invention. The ring members 10, 10a and 10b shown in FIGS. 1–3 have a generally "D-shaped" configuration which corresponds to the normal anatomical shape of the mitral valve annulus during closure. In the annulus, a straight portion is formed by the attachment of the anterior leaflet. It will be appreciated that if these ring members 10, 10a and 10b were intended for use in remodeling of the tricuspid valve, they would have the generally egg-shaped configuration of the normal anatomical shape of the tricuspid valve annulus, with a portion of the annulus being tough and a portion being flexible.

The ring member 10 shown in FIG. 1 comprises first 12, second 14 and third 16 tubular segments. Each segment 12, 14, 16 is coupled to the two other segments to form a substantially unitary ring structure. The first segment 12 is tubular in configuration, having open ends A and B into which the corresponding ends of the second and third segments 14, 16 are inserted. The second segment 14 has a blunt tipped or closed first end C and an open tubular second end D. The third segment 16 has blunt tipped or closed first and second ends E and F, respectively.

The segments include integrally formed coupling structure on adjacent ends to link the segments in a chain and define the periphery of the ring. The first end C of second segment 14 is inserted into the open second end B of the first segment 12. A series of raised lugs or teeth 18a protrude from one side of the portion of the second segment 14 which inserts into the second end B of the first segment 12. A corresponding series of apertures or detents 20a is formed in the side walls of the first segment 12. The individual teeth 18a snap into and frictionally engage the individual detents 20a, as shown.

Similarly, the first end E of the third segment 16 is inserted into the open second end D of the second segment 14. A series of raised lugs or teeth 18b protrude from one side of the portion of the third segment 16 which inserts into the first end A of the first segment 12. A corresponding series of apertures or detents 20c is formed in the side wall of the first segment 12. The individual teeth 18c snap into and frictionally engage the individual detents 20c, as shown.

The individual teeth 18 are configured and constructed such that upon application of an enlarging force, the segments 12, 14, 16 will spread apart and the teeth 18 will be caused to move out of the detents 20 within which they are positioned and will slidably advance and snap into the next available detent in the series, thereby effecting one incremental increase in the annular size of the ring. Further application of an enlarging force will cause the teeth 18 to move to the next available detents 20 in the series, thereby effecting a second incremental increase in size, and so on. After an incremental expansion, the teeth 18a, 18b, and 18c are shaped to prevent contraction of the ring member 10. This is necessary to provide structural support for the constantly flexing annulus to avoid collapse thereof.

A suture ring 38, formed of material such as a woven polyester mesh, is mounted about the periphery of the ring member 10, 10a and 10b to facilitate suturing-in-place of the ring member 10, 10a and 10b to surrounding anatomical tissue.

FIG. 2 shows an alternative ring 10a comprising first and second semi-annular tubular segments 30, 32 which are joined together in end to end fashion, as shown, to form the desired annular configuration of the ring 10a. Rack bars 34, 36 insert into the opposing ends of the first and second tubular segments 30, 32. Teeth 18 protrude laterally from the portions of each rack bar 34, 36 which insert into the juxtaposed ends of the first and second semi-annular tubular segments 30, 32 as shown. Corresponding apertures or detents 20 are formed in the side walls of the tubular members 30, 32. The individual teeth 18 snap into and frictionally engage the individual detents 20, as shown.

It will be appreciated that the components which make up the ring member 10 need not necessarily be of tubular configuration as shown in the embodiments of FIGS. 1 and 2. Indeed, as shown in FIG. 3, the ring member 10b may comprise a plurality of non-tubular arcuate leaves 40, 42, 44, 46 assembled in overlapping relation to one another and contained within a distensible outer sheath 48, as shown. In this particular embodiment, each leaf 40, 42, 44, 46 includes coupling structure formed thereon for cooperating with complementary structure on another leaf to allow expansion of the ring 10b but restrict contraction thereof In the illustrated embodiment, this coupling structure includes ratchet teeth 18 and detents 20.

As mentioned above, the application of an enlarging force to the ring 10a causes the semi-annular tubular segments 30, 32 to move apart and the individual teeth 18 to advance, and seat within, the next available detents 20, thereby increasing the size of the ring 10a by a predetermined incremental amount. The enlarging force may derive from manually applied dilatory pressure, or from tensile forces on the ring applied by growth of the patient's annulus. The former method of manual application of a dilatory pressure is now described in the context of a balloon catheter. Those of skill in the art will recognize, however, that there are other surgical methods for applying an enlarging force to the annuloplasty ring of the present invention.

Surgical Annuloplasty Ring Expansion

Figure 4:
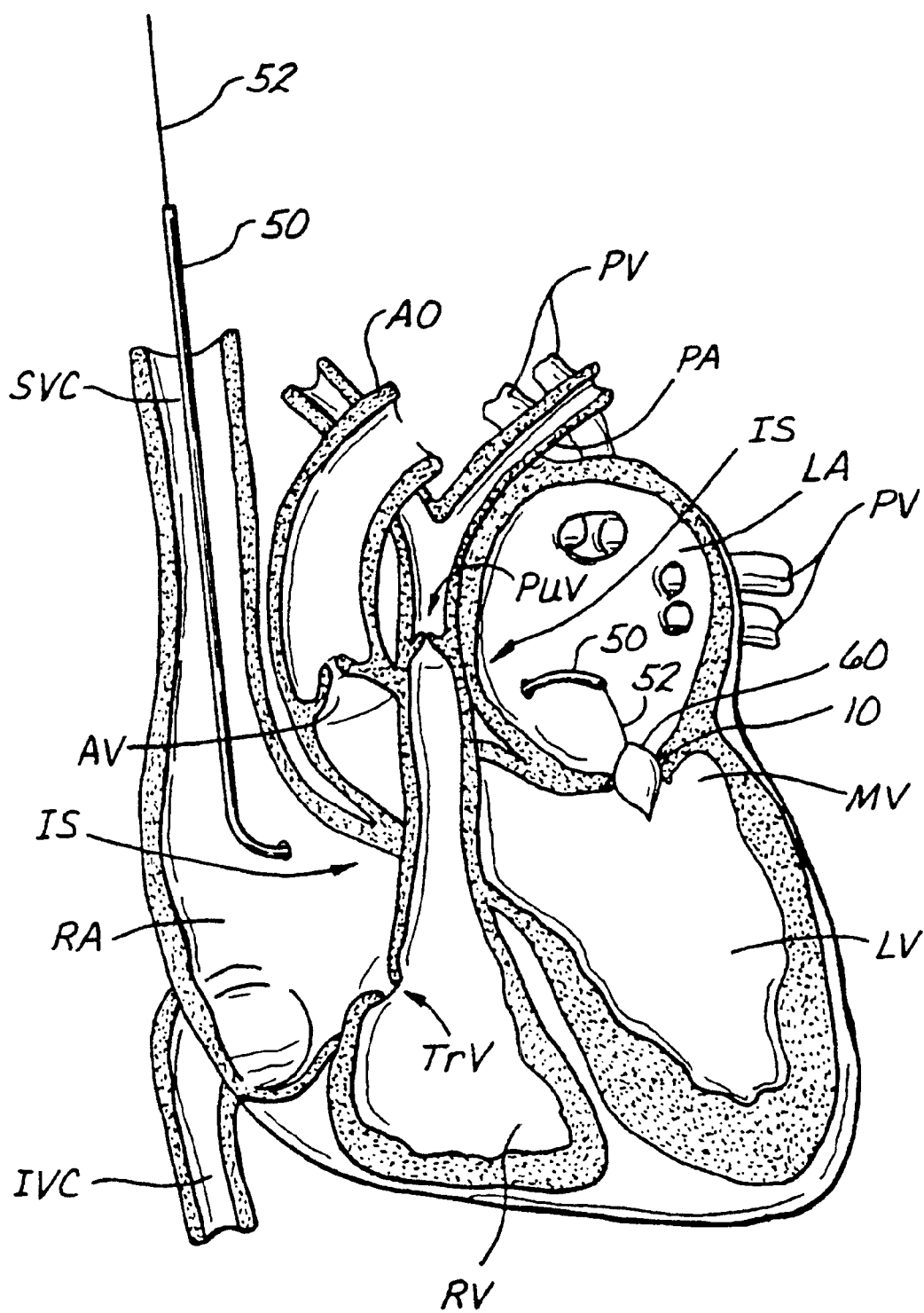
FIG. 4 is a sectional illustration of a human heart having an adjustable annuloplasty ring of the present invention implanted at the mitral position, and showing the manner in which a dilation apparatus (e.g., a balloon catheter or expandable cage) may be advanced through a catheter, positioned transeptally, and utilized to effect in situ enlargement of the adjustable annuloplasty ring in accordance with the method of the present invention.

FIG. 4 shows schematic illustration of the human heart having an adjustable annuloplasty ring 10 of the present invention implanted at the mitral position therein. The anatomical structures and major blood vessels of the heart are labeled, on FIG. 4, in accordance with the following legend:

| | |
|---|---|
| PV | Pulmonary Veins |
| PA | Pulmonary Artery |
| SVC | Superior Vena Cava |
| IVC | Inferior Vena Cava |
| AO | Aorta |
| RA | Right Atrium |
| RV | Right Ventricle |
| LA | Left Atrium |
| LV | Left Ventricle |
| IS | Interatrial Septum |
| AV | Aortic Valve Position |
| MV | Mitral Valve Position |
| TrV | Tricuspid Valve |
| PuV | Pulmonic Valve |

As shown in FIG. 4, the size of the annuloplasty ring 10 may be adjusted through introduction of a guide catheter 50, via catheterization of the superior vena cava such that the distal end of the catheter is passed through the interatrial septum IS, using known septal penetration technique, and into the left atrium LA. A balloon dilation catheter 52, such as a valvuloplasty catheter of the type commercially available, is then advanced through the lumen of the guide catheter 50, and positioned such that the balloon 60 of the balloon catheter 52 is within the annulus of the mitral valve MV. Thereafter, the balloon 60 is inflated, as shown, to, cause the adjustable annuloplasty ring 10 to expand to a larger annular configuration.

In embodiments, such as those described and shown here above in FIGS. 1–3, it will be appreciated that the balloon 60 may be expanded to a specific diameter which will evoke a single incremental increase (i.e., from one notch to the next) of the mechanical expansion-controlling system of teeth and notches formed in the annuloplasty ring 10.

Similarly, when the annuloplasty ring 10 is implanted at the tricuspid valve TrV it will be desirable to advance the guide catheter 50 through the superior vena cava SVA to a point where the distal end of the guide catheter 50 is positioned within the right atrium RA of the heart. The balloon dilation catheter 52 is then advanced to a point where the distal portion of the balloon catheter 52 extends through the tricuspid valve TrV. Thereafter, a balloon 60 will be dilated so as to expand an annuloplasty ring of the present invention (not shown) when implanted within the tricuspid valve TrV.

Natural Annuloplasty Ring Expansion (Self-Expansion)

In a preferred method of adjustment of the annuloplasty ring 10, no surgical intervention is necessary. In one example, a ring 10 having a major dimension of 20 mm is implanted in a child. Over the developing years, the patient's annulus may grow to a size of 24 mm or larger. As the annulus grows, the ring 10 accommodates this growth by incrementally increasing in size. The number of incremental size increases depends on the number individual teeth 18 and detents 20, but is desirably at least two and no more than four. In one specific example, therefor, two teeth 18 and associated detents 20 are provided at the junction of each ring segment and the ring is incrementally expansible in two to four stages from 20 mm to 24 mm.

Alternative Closed, Ratcheted, Segmented Annuloplasty Rings

Figure 5:
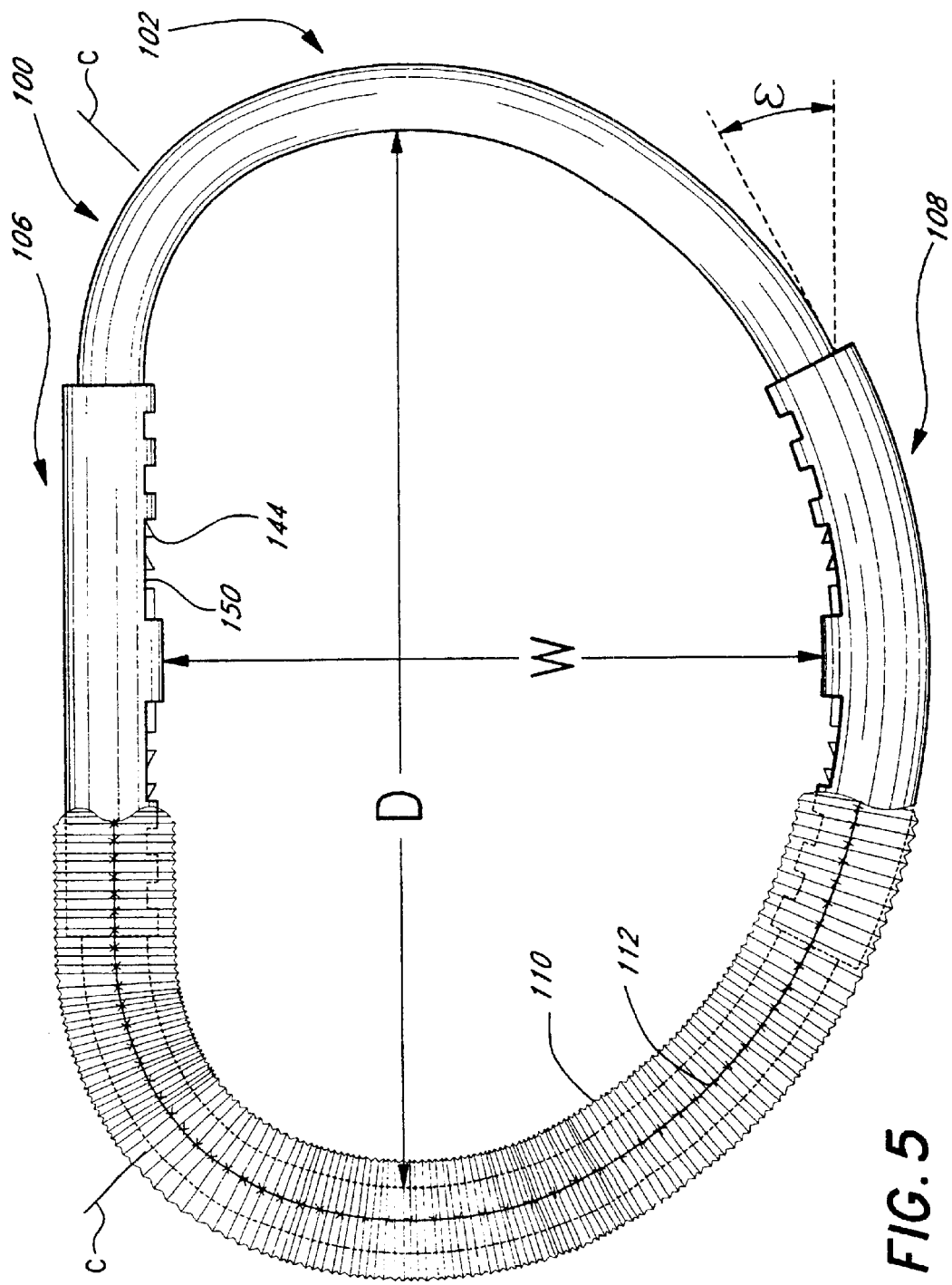
FIG. 5 is a plan view of a further embodiment of an adjustable annuloplasty ring of the present invention showing an outer suture covering partially removed to expose an inner ring structure.
Figure 6:
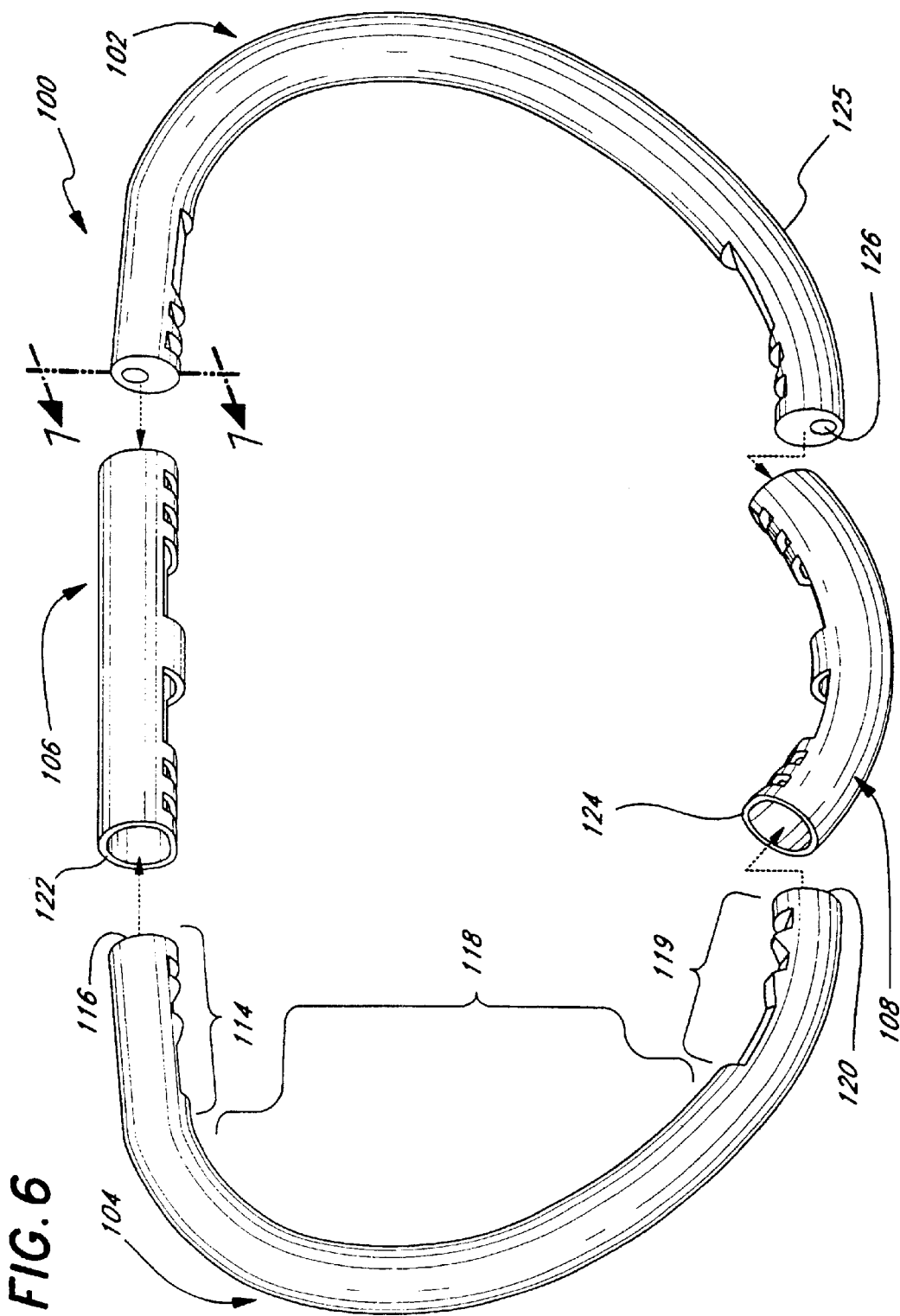
FIG. 6 is a perspective exploded view of the annuloplasty ring of FIG. 5 with the outer suture covering removed.

FIGS. 5 and 6 illustrate another embodiment of an adjustable annuloplasty ring 100 comprising a pair of identical ring segments 102 and 104 joined by a first coupling tube 106 and a second coupling tube 108. The annuloplasty ring 100 includes an outer fabric covering 110 having a circumferential seam 112 (partially shown in FIG. 5). The covering 110 functions as a sewing ring for the annuloplasty ring 100. As with the earlier described embodiments, the annuloplasty ring 100 has a generally D-shape with a length dimension D and a width dimension W. The shape of a mitral annulus is sometimes given in terms of its aspect ratio, or the width W over the length D. A preferred aspect ratio is about ¾, although certainly not all healthy anatomies conform to this ratio.

Commissures C are shown at opposed ends of a straight portion of the ring 100. The commissures C delimit the relatively straight area of attachment of the anterior mitral leaflet. This forms a tough fibrous edge on the inner septal wall as contrasted with outer flexible muscular portions of the mitral valve annulus. Generally, growth of the annulus occurs in the muscular portions, while the fibrous edge experiences minimal growth. Natural or self-expansion of the ring is therefore caused by outward growth generally along the axis of the straight portion, and growth radially outward around the curved portions. As will be clear from the description below, the construction of the adjustable ring 100 takes this natural growth into account and expands concurrently with minimal stress on attaching sutures.

With reference to FIG. 6, each of the ring segments 102 and 104 comprises a short straight portion 114 terminating in a free end 116, and a longer curvilinear portion 118 terminating in a short curvilinear portion 119 and free end 120. The ends 116 and 120 will be referred to hereafter as the straight end and curved end, respectively. The first coupling tube 106 is straight and includes opposed open mouths 122 within which are received the straight ends 116 of the ring segments 102 and 104. In this regard, the ring segments 102, 104 are mirror images of each other across the width axis of the ring, with their free ends 116 and 120 facing each other. The second coupling tube 108 is curvilinear, conforms to the shape of the short curvilinear portions 119 of the ring segments 102 and 104, and includes opposed open mouths 124 for receiving the curved ends 120.

Each of the ring segments 102 and 104 comprises a generally cylindrical composite rod having an exterior portion 125 surrounding an interior stiffener 126. Preferably, the exterior portion 125 is made of ultra-high molecular weight resin polymer. More preferably, the exterior portion 125 is made of a polyacetal, polyethylene, or. an acetal resin. The interior stiffener 126 is preferably made of a metallic rod such as titanium or Elgiloy®. The first and second coupling tubes 106 and 108 are preferably made of Elgiloy®, titanium, or other biocompatible metal.

The curvature of the second coupling tube 108 and the curvilinear portion 118 is shown with respect to a horizontal axis in FIG. 5. For purposes of orientation, the horizontal axis is parallel to the length dimension D. More particularly, a line tangent to the curve at the point at which the ring segment 102 extends within the coupling tube 108 makes an angle $\epsilon$ with the horizontal. This angle is important for maintaining a preferred shape, or aspect ratio, for the annuloplasty ring 100 upon expansion, as described below.

As with the embodiments of FIGS. 1–3, the annuloplasty ring 100 is adjustable in size. When the ring 100 is assembled for implantation, the straight ends 116 and curved ends 120 extend within respective tubes 106 and 108 as seen in FIG. 5. From this position, the ring segments 102 and 104 may gradually retract from within the tubes 106 and 108 by an external or host-generated force. More particularly, the annuloplasty ring 100, as with the annuloplasty ring described previously, may be expanded upon application of a dilatory force from a balloon catheter, or may be expanded upon growth of the patient's annulus. In the latter situation, the annuloplasty ring 100 is self-expanding and a further procedure to extend a balloon catheter within the ring is unnecessary. As the patient's annulus grows from childhood, the annulus grows and the ring 100 gradually expands therewith.

As the ring is dilated or otherwise expands, the preferred D-shape is retained due to the angle ε shown in FIG. 5. That is, the straight ends 116 begin retracting from the first coupling tube 106 along a common axis, while the curved ends 120 retract from the second coupling tube generally along a common curve. Thus, as the ring segments 102 and 104 pull apart and their ends retract from the respective coupling tubes 106 and 108, both the long dimension D and the width dimension W increase. The preferred angle ε ensures that these dimensions increase proportionally to maintain approximately the aspect ratio shown in FIG. 5. For example, an expandable ring 100 having an aspect ratio of ¾ may have an initial length dimension D of 16 mm, with a width W of about 12 mm. Upon expansion, the length D increases to 24 mm, while the width W increases to about 18 mm. The maximum expansion of the ring 100, as well as other telescoped rings, may be limited by the need for an initially overlapping structure. Preferably, the telescoped rings will have the capacity for expanding at least 4 mm in the length dimension.

The angle ε is a function of the length of the second coupling tube 108 and the curvature thereof which conforms to the curvature of the portion 119 of the ring segments 102 and 104. It should be noted that the portions 119 of the ring segments 102, 104 may not have a uniform curvature along their length, and the overall proportional shape or aspect ratio of the ring 100 may change slightly by an insignificant degree.

Structure for Regulation of Annuloplasty Ring Expansion

The structure for regulating the displacement of the ring segments 102, 104 with respect to the coupling tubes 106 and 108 will be described with reference to FIGS. 7 and 8. FIG. 7 is a cross sectional view of the straight end 116 of the ring segment 102, as taken along the sectional line shown in FIG. 6. The interior stiffener 126 is shown embedded within the exterior portion 125. It can be seen that the interior stiffener 126 is positioned off center with respect to the longitudinal axis of the ring segment 102 to accommodate the expansion regulating structure described herein. More particularly, the expansion regulating structure includes a series of grooves extending along the ring segment 102 from the straight end 116. Beginning closest to the straight end 116, a terminal groove 128, an intermediate groove 130, and an elongated groove 132 of identical depth are formed in series. The elongated groove 132 has a length approximately twice the length of the terminal groove 128 or intermediate groove 130. A secondary tooth 134 divides the terminal groove 128 from the intermediate groove 130. The secondary tooth 134 includes an angled front face 138 on the side of the intermediate groove 130, and a back face 136 extending generally perpendicularly to the axis of the ring segment 102 on the side of the terminal groove 128. A primary tooth 140 separates the intermediate groove 130 from the elongated groove 132, and includes a front face 144 and a back face 142. A stop face 146 defines an end of the terminal groove 128 opposite the secondary tooth 134, and a stop face 148 defines an end of the elongated groove 132 opposite the primary tooth 140. The curved ends 120 of the ring segments 102, 104 desirably include an arrangement of alternating teeth and grooves similar to the straight end 116 for mating with the second coupling member 108.

The front face 144 forms a shallower angle with respect to the longitudinal axis of the straight end 116 than does the front face 138 of the secondary tooth 134. In a preferred environment the front face 144 makes an angle α of about 30° with respect to the longitudinal axis, while the front face 138 of the secondary tooth 134 makes an angle β of about 45°. It will also be noted that the height of the primary tooth 140 with respect to the adjacent grooves is slightly less than the height of the secondary tooth 134 with respect to its adjacent grooves. Furthermore, the secondary tooth 134 is thicker in the axial direction than the primary tooth 140. The effects of the differing face angles, heights, and thicknesses of the teeth 134 and 140 on the ring expansion will be described in greater detail below. It should be noted, however, that the relative sizes and shapes of the teeth 134 and 140 are given by way of example only, and numerous variations will be readily apparent by one of skill in the art from the functional discussion below.

FIG. 8 illustrates one end of the first coupling tube 106 terminating in the open mouth 118. The coupling tube 106 includes structure for mating with the aforementioned teeth and grooves formed on the ring segment 102. More specifically, a plurality of apertures separated by bridges is formed on the end of the coupling tube 106, the apertures receiving the teeth on the ring segment 102. An elongated aperture 150 is formed farthest from the open mouth 118, a first detent 152 is formed slightly closer to the open mouth, and a second detent 154 is closest to the open mouth 118. The length of the elongated aperture 150 is approximately twice the length of both the first and second detents 152 and 154, respectively. A first bridge 156 separates the elongated aperture 150 from the first detent 152 and includes a contact edge 157 facing away from the open mouth 118. A second bridge 158 separates the first detent 152 from the second detent 154 and includes a contact edge 159, again facing away from the open mouth 118. A third bridge 160 separates the second detent 154 from the open mouth 118, and forms a part of the open mouth. It can readily be seen that the main portion of the coupling tube 106 is tubular in shape, with the bridges 156, 158 and 160 being somewhat flattened. In a preferred manufacturing step, the bridges begin as tubular walls and are flattened into the illustrated shape after forming the aperture 150 and detents 152 and 154, and after insertion of the ring segments 102, 104. The second coupling tube 108 includes a similar arrangement of apertures and bridges for mating with the curved ends 120 of the ring segments 102, 104. Of course, those of skill in the art will see that the expansion regulating structure between the first coupling tube 106 and ring segments 102, 104 and the second coupling tube 108 and ring segments may differ depending on performance requirements.

The interaction of the teeth and grooves of the ring segments 102 and 104 and the apertures and bridges of the coupling tube 106 will now be described, with the understanding that the same applies equally to the interaction with the second coupling tube 108. With reference to FIG. 6, the straight ends 116 of the ring segments 102 and 104 are initially inserted within the open mouths 122 of the first coupling tube 106. In this step of assembly, the flattened bridges 156, 158 and 160 have not yet been formed so that the coupling tube 106 between the mouths 122 is entirely tubular. Each straight end 116 extends far enough within the coupling tube 106 so that the primary tooth 140 projects and is visible from the elongated aperture 150, as seen in FIG. 5. Subsequently, the first, second and third bridges 156, 158 and 160 are deformed into their flattened shape as shown in FIG. 8 using metal forming tools and anvils well known in the art. The grooves formed in the ends of the ring segments 102, 104 accommodate the bridges.

Following this operation, the straight ends 116 of the ring segments 102 and 104 are captured within the tube 106. That is, the primary tooth 140 is sized to interfere with the contact edge 157 formed by the first bridge 156. Likewise, a similar operation captures the curved ends 120 within the second coupling tube 108. Therefore, the ring segments 102 and 104 are effectively captured within the tubes 106 and 108 to form the D-shaped ring 100. It should be noted that although the elongated aperture 150 is shown large enough to expose both the primary tooth 140 and secondary tooth 134, it need only be large enough to separate and define the first bridge 156 so as to create an interference between the contact edge and the primary tooth. The minimum size of the ring 100 is limited by either contact between the stop face 148 and the mouth 122, or by contact between the straight ends 116 of the ring segments 102 within the coupling tube 106.

Regulated Annuloplasty Ring Expansion

The annuloplasty ring 100 is then surgically implanted within the annulus of the patient using well known techniques with the sewing ring or covering 110 secured to the annulus with sutures. After a number of months or years, a balloon catheter may be introduced into the patient's venous system to enlarge the ring 100. In a preferred embodiment, however, the ring 100 self-expands upon application of natural annulus growing forces. More specifically, the growth of the annulus pulls the ring segments 102, 104 away from each other and out of the coupling tubes 106 and 108. As mentioned previously, growth of the annulus occurs in the muscular tissue areas outside of the straight portion of the ring 100 defined between the commissures C. This area grows and applies tensile forces on the ring segments 102, 104 to eventually cause the primary teeth 140 to deform underneath and past the first bridges 156 into the first detents 152. When the primary teeth 140 clear the bridges 156, the back faces 142 prevent movement in the reverse direction and maintain the incremental size expansion. Over time, growth of the annulus acts on the ring segments to further expand the ring 100. The secondary teeth 134 deform underneath and past the first bridges 156, while the primary teeth 140 likewise are forced past the second bridges 158 into the second detents 154. The back faces 136 and 142 prevent movement in the reverse direction and maintain the incremental size expansion of the ring 100. Still further growth of the annulus eventually retracts the ring segments 102, 104 far enough from the coupling tubes 106, 108 to move the stop faces 146 against the contact edges 157 which limits the maximum expansion of the ring 100. In practice, though the annulus grows relatively symmetrically around its periphery (except for the fibrous septal wall), the ring 100 may be expanded upon interaction of one or more of the tooth/detent combinations before the others. Exact synchronism in this respect is not critical, however, and further natural annulus growth is expected to even out the peripheral ring expansion.

The initial free expansion of the ring segments is regulated by the interference between the primary tooth 140 and the first bridge 156. Ultimately, the force of growth of the annulus is great enough to deform the plastic tooth 140 underneath and past the first bridge 156. The initiation and ease of this deformation is partly regulated by the angle α of the front face 144. That is, the steeper the angle α the greater the resistance to deformation of the tooth 140. With a preferred angle of 30 degrees, for example, the amount of force needed to enlarge the ring 100 is relatively small. Additionally, the radial height of the primary tooth 140 in relation to the position of the bridge 156 affects the timing of and resistance to initial ring expansion. The taller the tooth 140, the more resistance to deformation, and thus the longer the period before expansion forces can enlarge the ring by forcing the tooth 140 under or completely past the bridge 156. Finally, the thicker the tooth 140 is in an axial direction the more resistance there will be to deformation. Design specifications for various ring configurations, and knowledge of patient characteristics enables the surgeon to select the proper expansible ring 100 in different situations. For example, the ring 100 shown in FIGS. 5–8 includes a primary tooth 140 that is shorter, thinner and has a shallower face angle than the secondary tooth 134. Thus, less expansion force is required to initially enlarge the ring 100 by deformation of the primary tooth 140 than is required to subsequently deform the secondary tooth 134 for a second incremental expansion. In addition, as mentioned above, the second incremental expansion must overcome not only the secondary tooth 134 and first bridge 156 interaction, but the primary tooth 140 interacts with the second bridge 158 and affects the force needed to expand the ring. A design in which the initial expansion is relatively easy and subsequent expansions become gradually more difficult is preferable for pediatric applications where the child's annulus is initially fairly weak, but increases in size and strength over the predicted implanted life of the ring 100. The force required to enlarge the ring 100 increases from the first increment to the second because of the differing teeth, while the strength capacity of the patient increases concurrently, so that the differences in periods between incremental expansions are reduced. This control of the expansion characteristics of the ring 100 enables the surgeon to better match rings to different patients.

Alternative Expansion Regulation Structure

FIG. 9 illustrates an alternative embodiment of a coupling tube 106' in which the first and second bridges 156' and 158' are severed at approximately their midpoint. Each bridge 156' and 158' includes a pair of walls extending from the tubular main body of the coupling tube 106' and terminating in opposed free ends 170 and 172, respectively. Thus, the first and second bridges 156' and 158' are effectively cantilevered from the tubular body. This configuration encourages more rapid expansion of the annuloplasty ring 100 upon application of natural annulus or balloon dilatation forces. That is, the primary tooth 140 deforms to some extent, but also forces the free ends 170 of the bridges outward. The third bridge 160 remains solid to provide a stop described above. Other variations of the coupling tubes 106 and 108 are contemplated to reduce, increase, or otherwise regulate the ease of retraction of the ring segments 102, 104 therefrom.

FIG. 10 illustrates a further alternative ring segment 180 and coupling tube 182. In this version, the coupling tube 182 includes an elongated aperture 183 for receiving one or more generally rounded bumps or protrusions 184 formed on the ring segment 180. The protrusions 184 interfere with the walls of the aperture 183 to nominally position the ring segment 180 with respect to the coupling tube 182. Again, as described above, external balloon or internal body forces pull the ring segment 180 in the direction of the arrow 185 so that a first protrusion cams underneath the walls of the elongated aperture 183 and into a detent 186. A number of the protrusions 184 and detents 186 may be provided for various levels of adjustability. Furthermore, and consonant with the discussion of the earlier embodiments, the wall angles of the protrusions 184, their width, height, and even the material or surface lubricity, may be varied to regulate the ease of relative ring segment 180 and coupling tube 182 displacement.

Expandable Fabric Covering

The sewing ring or covering 110 is designed to stretch with the expanding ring segments 102 and 104. The degree of stretchiness in sewing ring fabrics depends primarily on the weave and orientation thereof. Many different types of weaves are available, and custom designed or specified fabrics for use with the annuloplasty ring 100 can be obtained from textile design houses. Of course, such specifications may increase the expense of each ring considerably, and thus the present invention contemplates the modification of fabric used to cover conventional sewing rings to save expense. Specifically, FIG. 11 illustrates a conventional fabric tube 190 used for covering annuloplasty rings and other medical devices to provide an anchoring surface for sutures. The weave 192 of the tube 190 is typically such that flexibility in a radial direction is somewhat greater than in a longitudinal direction. Note that the weave 192 is illustrated schematically and should not be construed as an accurate rendition of any one stitch pattern.

FIG. 12 illustrates a fabric tube 194 having an identical weave 196 as the fabric tube 190 shown in FIG. 11, but of a significantly larger diameter. Again, the weave 196 is less stretchy in the axial or X direction as it is in the radial or Y direction (as indicated by the coordinate axis). A series of cut lines are formed in the tube 194 to provide individual tube segments 200, seen nearly completely surrounding the ring 100 in FIG. 13. These tube segments 200 are positioned around the annuloplasty ring 100 and sewn along the circumferential seam 112. In this manner, the orientation of the weave 196 is reversed from conventional sewing ring coverings. That is, the axis in which the weave 196 has maximum stretch is now oriented in a circumferential direction around the annuloplasty ring 100. This orientation accommodates growth or expansion of the ring 100 as the patient grows.

Discontinuous, Inelastic, Annuloplasty Rings

Figure 14:
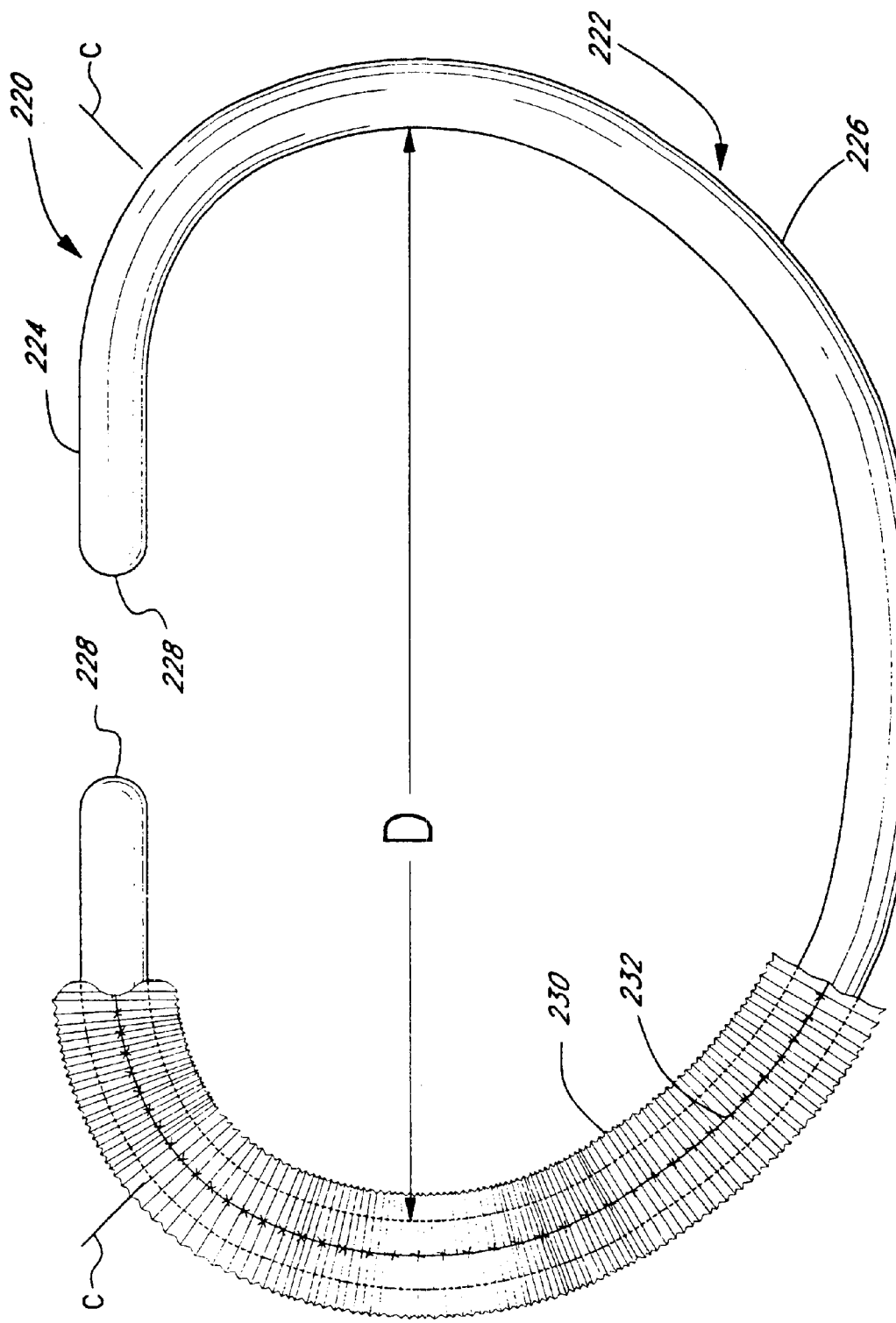
FIG. 14 is a plan view of an adjustable annuloplasty ring made of a single discontinuous, non-elastic segment and a suturable covering.
Figure 14A:
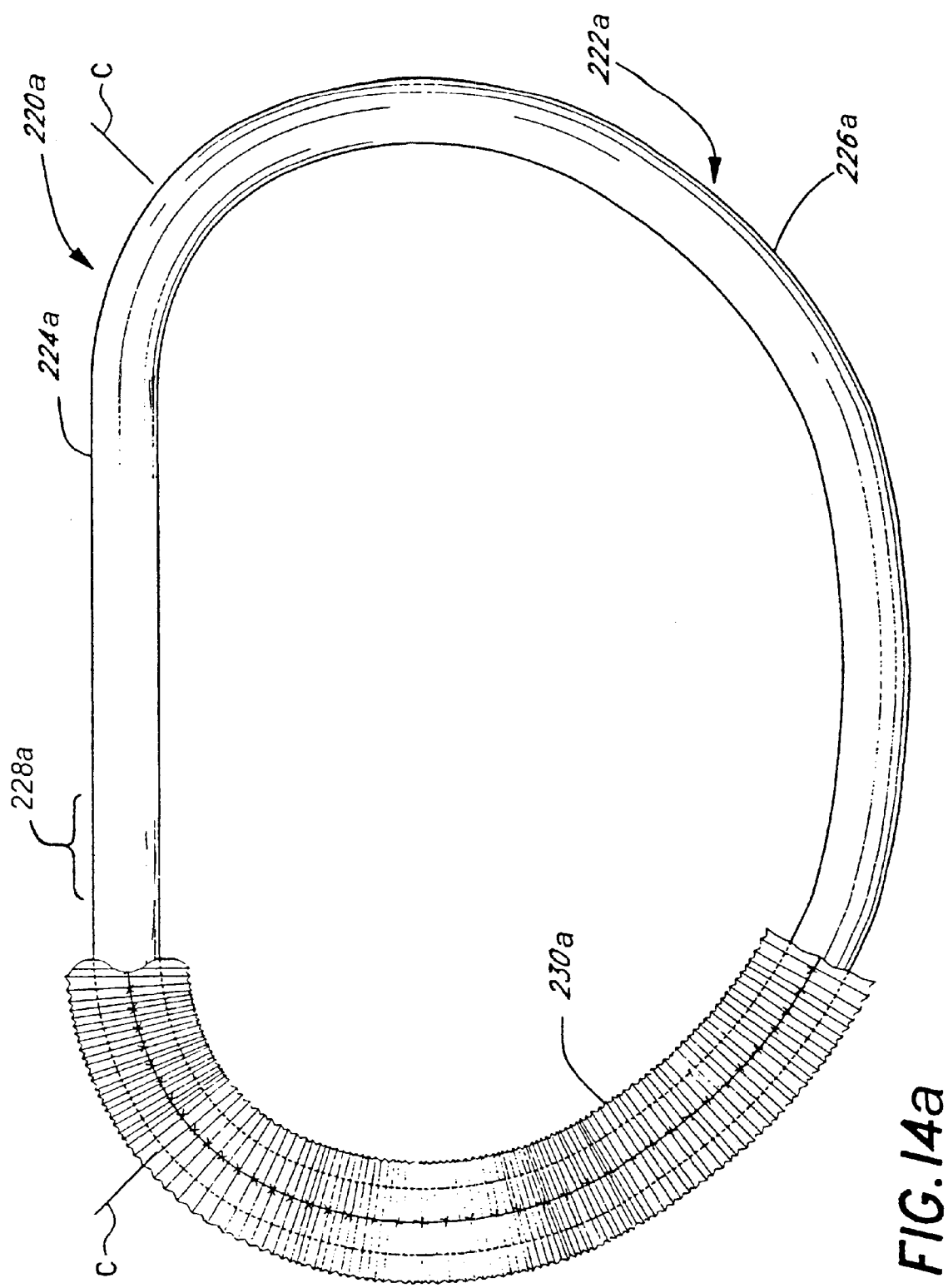
FIG. 14a is a plan view of an alternative adjustable annuloplasty ring made of a single discontinuous, non-elastic segment and a suturable covering.

FIG. 14 illustrates a still further embodiment of an adjustable annuloplasty ring 220 configured in accordance with the present invention. The ring 220 comprises a solid ring segment 222 having a straight section 224 and a curvilinear section 226, with the straight section forming free ends of the curvilinear section. The commissures C as described above are shown generally delimiting the straight section 224. The straight section 224 includes facing ends 228 so that the ring 220 is discontinuous, or open. The discontinuity may be positioned as shown in the middle of the side of the ring 222 connected to the fibrous septal tissue, or may alternatively be offset from this symmetric position. Preferably, however, the discontinuity is within the generally straight portion between the commissures C between which there is less growth. This ensures that a continuous segment of the ring 220 surrounds the muscular portions of the annulus. The discontinuity may be formed by a break in the ring periphery so that the ring is open. Alternatively, as illustrated in FIG. 14a, the discontinuity may be formed by a relatively weak or stretchable section of the ring 224a that includes the discontinuity 228a.

A fabric covering 230 surrounds the ring segment 222 and may have a longitudinal seam 232. The ring 220 is designed to grow in size along with the patient's annulus, or may be surgically enlarged such as with a balloon catheter described above with reference to FIG. 4. The segment 222 is preferably made of a material which creeps over time; that is, the material exhibits plastic deformation properties and may be, for example, a polyacetyl. In this embodiment, there is desirably no inner stiffening portion, as with the earlier embodiments. The ring 222 has sufficient pliability to spontaneously expand on growth of the annulus, and sufficient plasticity to retain the expanded shape and provide adequate support for the developing annulus.

Discontinuous, Segmented, Expandable Annuloplasty Rings

A further form of expandable annuloplasty ring of the present invention comprises segments which are flexibly joined together at junctions, and which do not form a continuous periphery (in other words, the ring is open). Some annuloplasty rings of the prior art are rigid and in one piece with a break in the periphery to conform to certain anatomical features (notably the midpoint along the connection point of the anterior leaflet in the mitral orifice, and at the anteroseptal commissure in the tricuspid orifice). However the rigidity of these designs prohibits any expansion upon natural growth of the annulus, or even if a balloon dilatation procedure was used. The present invention provides discontinuous rings which are segmented, so as to pivot with respect to one another at the junction regions. The segments are sufficiently long and coupled together in a manner such that the ring adequately supports the annulus, and corrects any defects. Because of the pivoting action, however, the ring expands with the growing annulus.

One primary benefit of constructing the expandable rings with a discontinuity is the wider capacity for expansion. That is, there is no initial constraint of providing overlapping structure, as in the telescoped versions of the ring. Therefore, theoretically, the ring could open up as wide as possible. Of course, a preferred aspect ratio of the ring should be maintained, and thus the expansion is limited in this regard. In one example, a segmented open ring 100 having an aspect ratio of ¾ may have an initial length dimension D of 20 mm, with a width W of about 15 mm. Upon expansion, the length D increases to 32 mm, while the width W increases to about 24 mm.

Figure 15A:
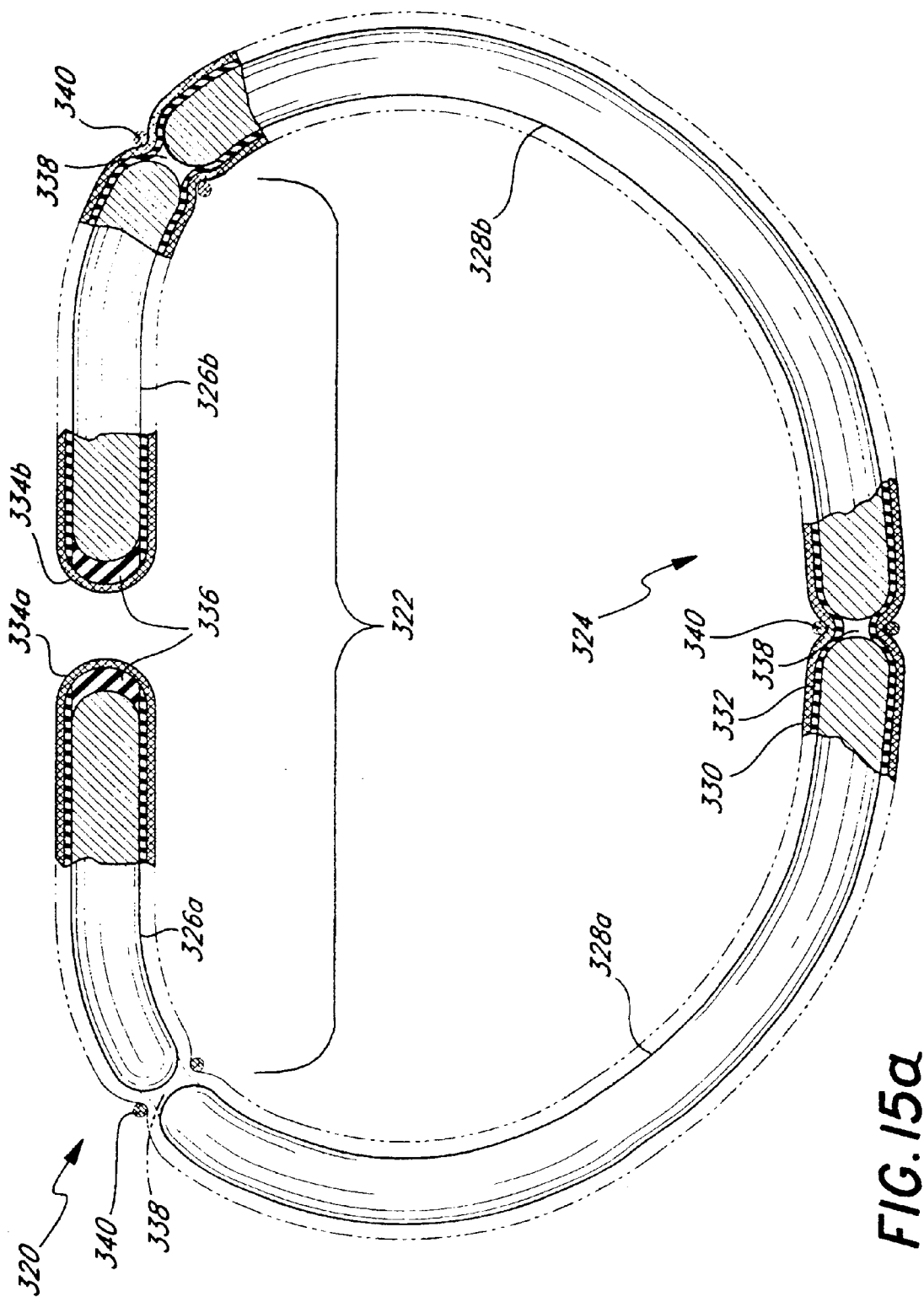
FIG. 15a is a partial sectional view of a four-part expandable annuloplasty ring of the present invention.

An exemplary embodiment of a four-part discontinuous, segmented, expandable annuloplasty ring 320 is seen in FIG. 15a. The ring 320 shown is intended for support of the mitral valve, and as such has a somewhat D-shape with a relatively straight side 322 and a convex portion 324 around the remaining periphery. The native mitral annulus is not a flat plane, and the anterior portion of the mitral annulus, which is relatively straight in plan view, extends out of a plane around which the posterior leaflet side extends. The straight side 322 of the ring 320 is thus designed to match the anterior portion of the mitral annulus, while the convex portion 324 conforms to the relatively planar posterior leaflet side.

The expandable annuloplasty ring 320 includes four main parts; two end segments 326a and 326b make up the straight side 322, while two curvilinear segments 328a and 328b define the convex portion 324. It should be noted that the end segments 326 are not entirely straight, and include slight curvatures to transition toward the curvilinear segments 328. A fabric covering 330 and a tubular sheath 332 encompass all four of the segments, which are not otherwise connected.

Each of the segments 326 and 328 desirably comprise solid cylindrical lengths of relatively rigid material, such as titanium, Elgiloy, a thermoplastic or other polymer, or other such biocompatible material. Alternatively, the segments 326 and 328 may be semi-rigid, and exhibit some elasticity or plasticity. The opposite ends of each of the segments 326 and 328 are preferably rounded to protect the other components of the ring from scoring or other abrasive damage in either assembly or use. Of course, those of skill in the art will recognize that other configurations of segments are possible, such as differing cross-sections, end shapes and the like.

In a preferred embodiment, the tubular sheath 332 extends from a first end 334a to a second end 334b of the ring 320.

The sheath 332 may be made of silicone, or other similar expedient and closely conforms to the exterior diameter of the cylindrical segments 326 and 328.

At the terminal ends 334a, 334b the sheath 332 extends generally axially beyond the ends of the cylindrical segments 326 to define a small cavity that is then filled with a biocompatible material 336, such as silicone. The fabric covering 330 extends around the ends of the tubular sheath 332 and filler material 336 and is stitched to close the ring ends 334a, 334b and provide a fabric covering around the entire exterior thereof.

The cylindrical segments 326 and 328 are spaced from one another within the tubular sheath 332 by small voids, such a shown at 338 of the bottom of FIG. 15a. Sutures 340 or other similar expedient are used to tighten the fabric covering 330 and tubular sheath 332 in the region of the voids 338. In this manner, the cylindrical segments 326 and 328 may easily pivot with respect to one another, but are generally secured from relative misalignment or longitudinal movement within the ring 320. The voids 338 thus define three pivot regions between the segments around the ring 320.

A break or discontinuity in the ring 320 is provided between the ring ends 334a, 334b, or in the anterior side of the ring. The discontinuity enables the ring 320 to expand and the segments to pivot with respect to one another. The open ring 320 can expand a substantial amount to accommodate growth of an annulus from a size of about 16 mm to an adult size of about 32 mm. In an alternative embodiment, the discontinuity in the ring is bridged by a member capable of great elongation, such as a length of stretchable material. In this manner, the ring is not "open" per se, but has a discontinuity in that one section is relatively more expandable than the remaining ring periphery.

Figure 15B:
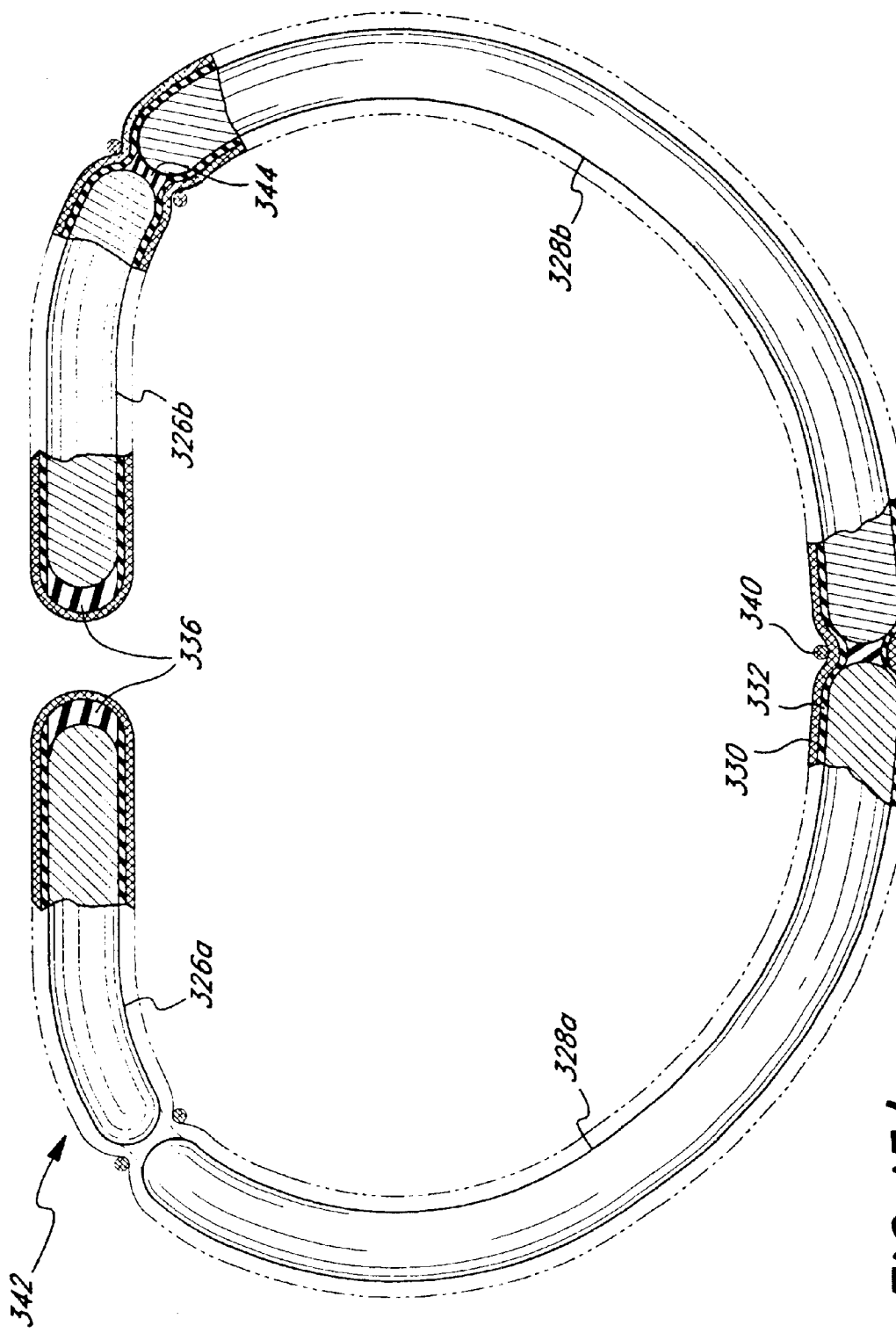
FIG. 15b is a partial sectional view of a further four-part expandable annuloplasty ring of the present invention.

In an alternative embodiment, an expandable annuloplasty ring 342 seen in FIG. 15b is substantially identical to the ring 320 of FIG. 15a, with the exception that the voids 338 previously disclosed are now filled with a pliable or otherwise soft material 344. The remaining elements of the ring 342 are given the same numbers as in FIG. 15a. Again, the filler material 344 may be an injectable silicone or other such biocompatible material. The filler material 344 is preferably injected through the fabric 330 and sheath 332 into the voids 338 after the segments 328 are positioned within the sheaths. The filler material 344 helps maintain a preferred shape of the ring 342 prior to implantation, and thus may be an aid for the surgeon. Of course, techniques of implantation using a rigid template are available, and would firmly maintain the ring shape regardless of the relative flexibility of the coupling regions.

Figure 16:
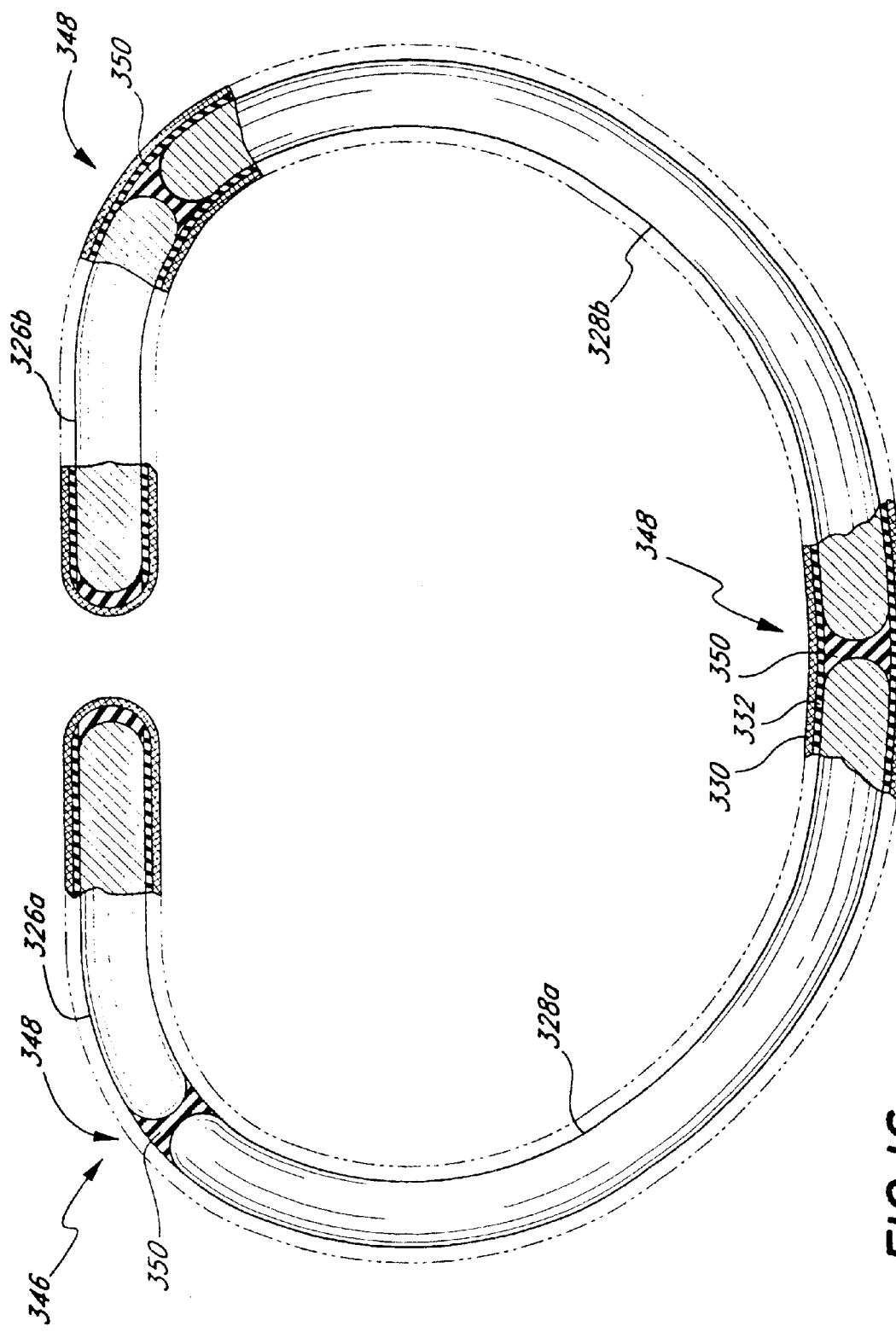
FIG. 16 is a partial sectional view of a still further four-part expandable annuloplasty ring of the present invention.

A still further embodiment of a four-part expandable annuloplasty ring is seen at 346 in FIG. 16. Again, many of the elements illustrated are similar if not identical with the elements seen in FIG. 15a, and thus wherever appropriate like numbers will be repeated. The ring 346 includes the relatively linear segments 326a, 326b, and the curvilinear segments 328a, 328b, as well as the continuous surrounding fabric covering 338 and sheath 332. In contrast to the first embodiments, there are no sutures pinching the material in the regions between the cylindrical segments 326 and 328. Instead, regions 348 include filler material 350 between the cylindrical segments. Because of the relative rigidity of the segments 326 and 328 in contrast to the pliable filler material 350, the regions 348 serve as pivot points for the annuloplasty ring 346.

Figure 17:
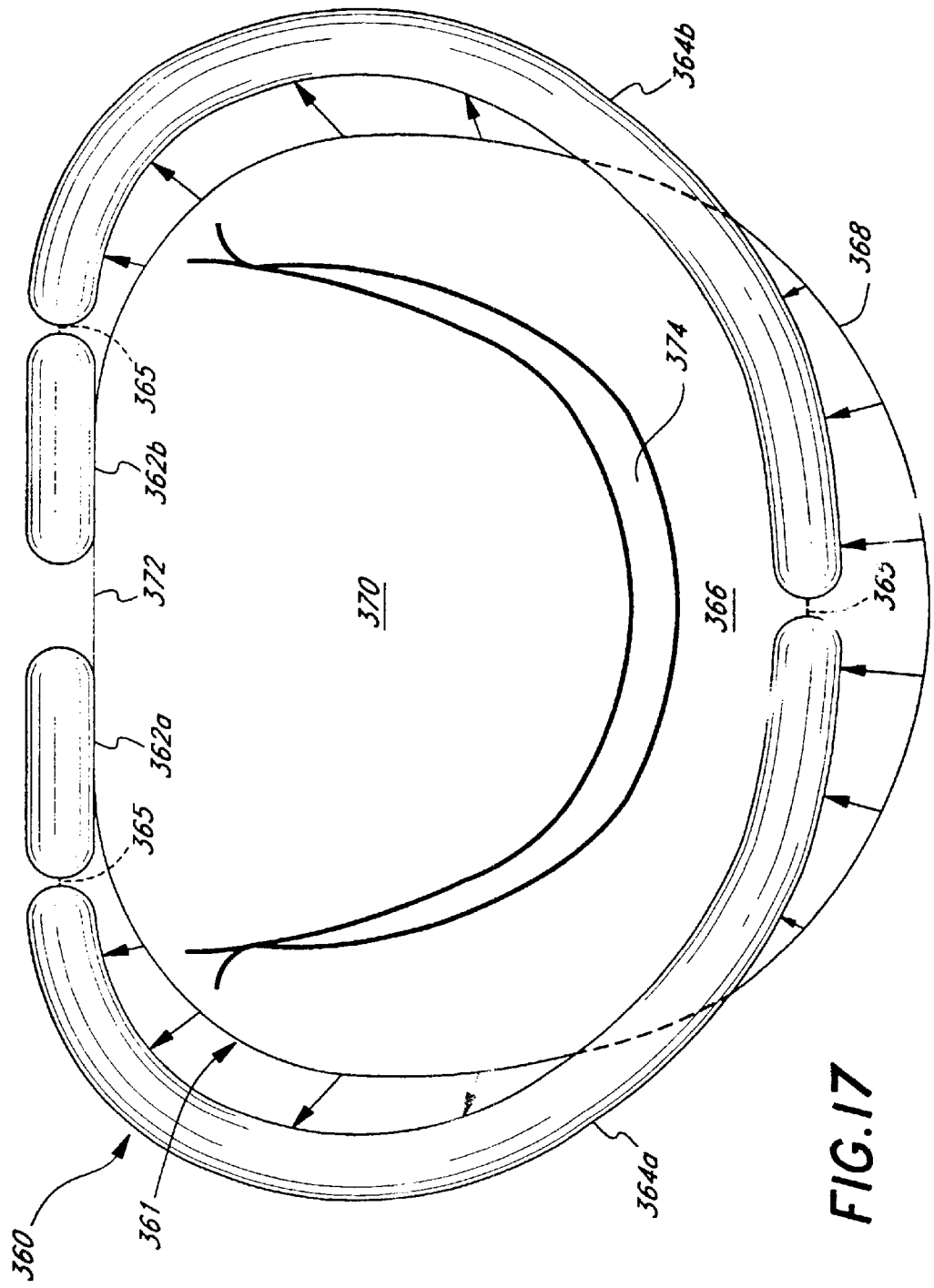
FIG. 17 is a schematic view of an alternative four-part expandable annuloplasty ring superimposed over a misshapen mitral valve annulus.

FIG. 17 schematically illustrates a four-part expandable annuloplasty ring 360 superimposed over a misshapen mitral annulus 361. Only the cylindrical segments of the annuloplasty ring 360 are shown for simplicity. In this regard, the ring 360 includes two straight segments 362a and 362b, as well as two curvilinear segments 364a and 364b. The ring 360 is a slightly modified form of the rings 320, 342 or 346 in that the straight segments 362 are shorter than before and entirely straight. The pivot regions between the segments 362 and 364 are schematically indicated by small dashed connecting lines 365, and may be formed of the voids or pliable filler material between the segments, or other structure as will be appreciated. The mitral annulus 361 comprises a posterior leaflet 366 attached around a convex posterior side 368, and an anterior leaflet 370 attached along a straight (in plan view) anterior side 372. As seen in FIG. 17, one potential deformation of the mitral annulus is relative widening in the anterior-posterior direction, accompanied by relative shortening in the transverse direction. As a result of the misshapen annulus there may be improper coaptation between the leaflets 364 and 368 and a gap 374 formed causing valvular insufficiency or regurgitation.

Figure 18A:
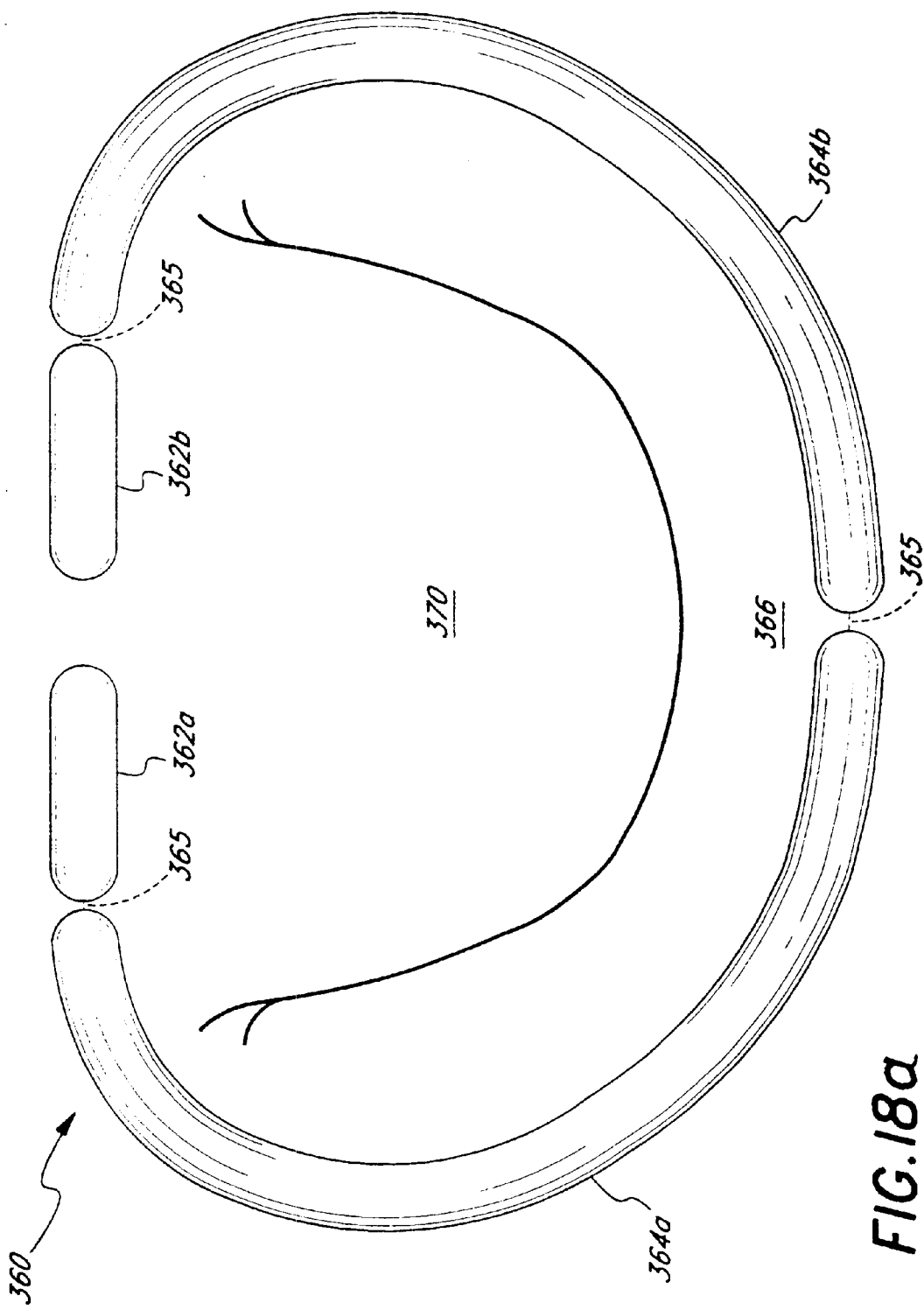
FIG. 18a is a plan view of the expandable annuloplasty ring of FIG. 17 after implantation to restore the proper shape to the mitral valve annulus.

To correct the valvular deficiency, the annuloplasty ring 360 is implanted around the annulus as seen in FIG. 18a. The arrows in FIG. 17 indicate the directions that the periphery of the annulus must move to implant the ring 360. Techniques for implanting annuloplasty rings are well known in the art and will not be described herein, other than to note that traditionally, evenly spaced sutures are used to join the fabric covering and adjacent tissue. After the annuloplasty ring 360 has been secured around the mitral annulus, the gap 374 shown in FIG. 17 disappears and the posterior leaflet 366 properly coapts with the anterior leaflet 370. The cylindrical segments 362 and 364 have sufficient rigidity to provide the proper physical support to the deficient annulus, and maintain its natural physiological shape. Although the pivot regions 365 permits some flexibility between the segments 362 and 364, the juxtaposed ends of adjacent segments are maintained in axial alignment, thus maintaining the desired shape of the annuloplasty ring 360. The annuloplasty ring 360 is initially sized for the not yet fully developed annulus.

FIG. 18b illustrates the same annuloplasty ring 360 as seen in FIGS. 17 and 18a, after growth of the mitral valve annulus 361. As can be seen from the drawing, the overall shape of the annuloplasty ring 360 remains substantially the same as when initially implanted, but the size has increased. More specifically, the left and right curvilinear segments 364a and 364b have spread out from one another, as permitted by the lower pivot region 365, and the discontinuity in the ring 360 provided in the anterior side between the opposing ends of the short segments 362a and 362b. In addition, the short segments 362 have pivoted slightly outward with respect to the curvilinear segments 364, as permitted by the pivot regions 365 therebetween. The end result is that the mitral valve annulus 361 remains properly supported by the annuloplasty ring 360, with the leaflets 366 and 370 maintaining good coaptation with no gap therebetween.

Figure 18C:
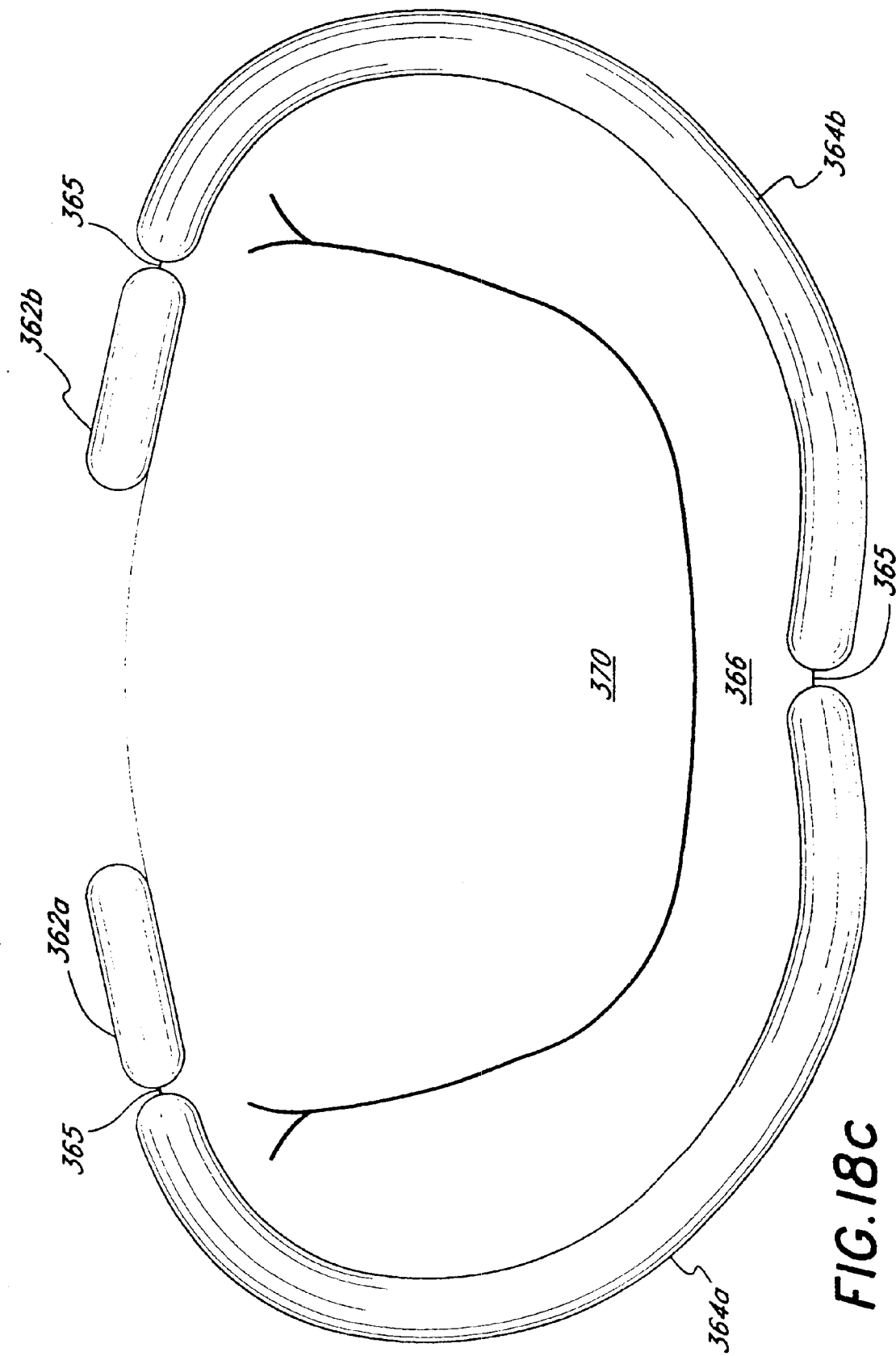
FIG. 18c is a plan view of the annuloplasty ring of FIG. 18a after further elapsed time and growth of the mitral valve annulus.

In a final view of the sequence of growth of the mitral valve annulus 361, FIG. 18c illustrates the annuloplasty ring 360, which has expanded from the size of FIG. 18b, maintaining proper anterior/posterior geometry. Again, the curvilinear segments 364 have further spread apart about the lower pivot region 365, while the short linear segments 362 are permitted to pivot with respect to the curvilinear segments. The mitral valve annulus 361 is properly supported so that the leaflets 366 and 370 meet with good coaptation.

Figure 19:
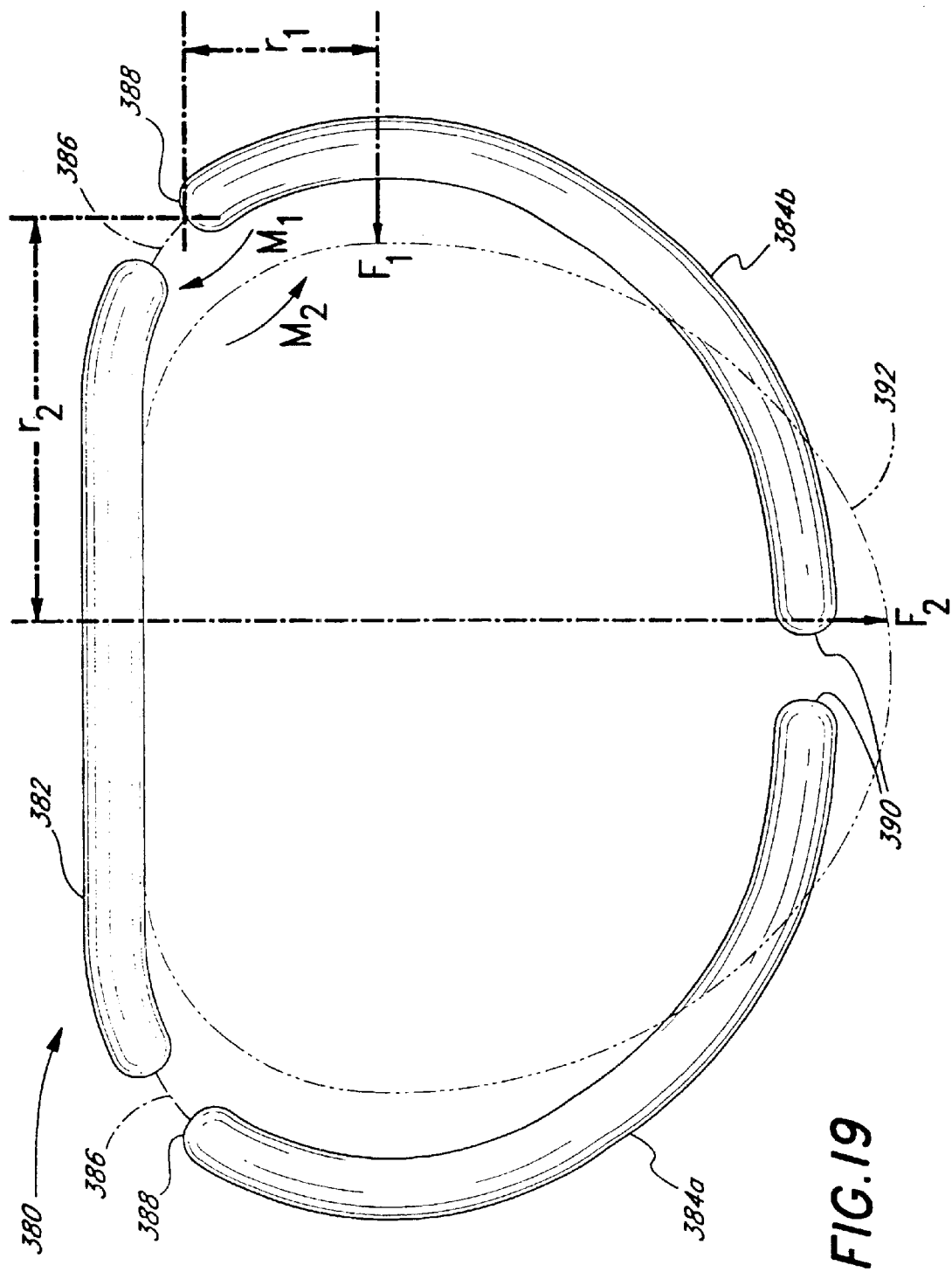
FIG. 19 is a plan view of an embodiment of a three-part expandable annuloplasty ring of the present invention illustrating certain force and moment conventions.

With reference now to FIG. 19, a three-part embodiment of a discontinuous, segmented, expandable annuloplasty ring is shown. The three-part annuloplasty ring 380 comprises a generally linear segment 382 and two curvilinear segments 384a and 384b. The generally linear segment 382 is pivotally coupled to the curvilinear segments 384 at pivot regions 386. More specifically, a first end 388 of each of the curvilinear segments 384 is pivotally coupled to one of the ends of the generally linear segment 382. A break or discontinuity in the ring 380 is formed between the second ends 390 of each of the curvilinear segments, or around the posterior side of the ring. The discontinuity allows the curvilinear segments to spread apart with respect to one another.

The annuloplasty ring 380 is shown superimposed over a misshapen mitral valve annulus 392, seen in dashed line. As with the four-part annuloplasty ring 360 of FIGS. 17 and 18, upon implantation using a number of well known surgical techniques the three-part annuloplasty ring 380 corrects the misshapen annulus 392. The generally linear segment 382 is implanted along a portion of the annulus to which the anterior leaflet attaches. This portion is generally considered to be more fibrous and less flexible than the remaining periphery of the annulus. The curvilinear segments 384, on the other hand, are implanted around the posterior side of the annulus that comprises flexible muscular tissue and is subject to a larger growth rate than the anterior side. Therefore, over time, the generally linear segment 382 is relatively stable, while the curvilinear segment 384b spreads outward with the growing annulus and pivots about its first end 388, as permitted by the pivot region 386.

As will be understood by those of skill in the art, correction of a mitral valve annulus such as a shown in the dashed line 392 imposes certain forces on the curvilinear segment 384b. FIG. 19 illustrates force and moment conventions imposed on the curvilinear segment 384b after implantation and correction of the mitral valve annulus. More particularly, the transverse dimension of the annulus 392 perpendicular to the anterior-posterior dimension is increased upon implantation of the ring 380. Stretching the tissue outward in this manner tends to impose an inward force on the curvilinear segments 384 as shown by the force arrow $F_1$. $F_1$ is shown acting along an axis of greatest transverse dimension of both the annulus 392 and a ring 380. Conversely, the anterior-posterior dimensions of the annulus 392 is reduced upon implantation of the ring 380, which tends to impose an outward spring force on the ring along that axis. That force is represented by the force arrow $F_2$ acting outward at the second end 390 of the curvilinear segment 384b. Of course, in reality the forces imposed on the ring 388 by the corrected annulus 392 are distributed more evenly than the summed forces shown, which are used for purposes of clarity to illustrate the preferred design of the annuloplasty ring 380.

Assuming the curvilinear segment 384b pivots about the first end 388, the force $F_1$ acts along a moment arm having a length $r_1$, thus setting up moment $M_1$. At the same time, the force $F_2$ acts along a moment arm having a length $r_2$, thus setting up a counter-balanced moment $M_2$. The two moments $M_1$ and $M_2$ cancel each other now so that the annuloplasty ring 380 retains its initial pre-implantation shape. In other words, the ring 380 is designed so that the moments imposed on it after implantation and beyond are in equilibrium, to ensure the initial ring shape is maintained. Furthermore, the material of the curvilinear segments 384 are of sufficient rigidity to prevent bending.

It should be noted that the precise forces imposed on the annuloplasty ring 380 after implantation in any particular patient cannot be determined with great accuracy prior to surgery, and then only with careful measurements, which may be impractical. To estimate the forces that may be imposed on the ring 380, a body of empirical data regarding misshapen mitral valve annuli in combination with careful geometric design considerations would be useful. Such data regarding the forces imposed by mitral valve annuli may be obtained from studying animal subjects with similar anatomical features, such as pigs, or by studying human subjects during autopsy. Ultimately, the data should enable those skilled in the art to predict the forces associated with correcting a misshapen annulus, and design the annuloplasty ring accordingly. Such research may spur the design of a number of different expandable ring configurations with gradually varying pivot locations, for example, to enable the surgeon to find a best match for the particular valvular deficiency. Indeed, the discussion with respect to forces and moments imposed on a three-part annuloplasty ring, such as shown in FIG. 19, applies equally to the four-part rings as shown earlier, and other configurations of expandable arinuloplasty rings.

Figure 20:
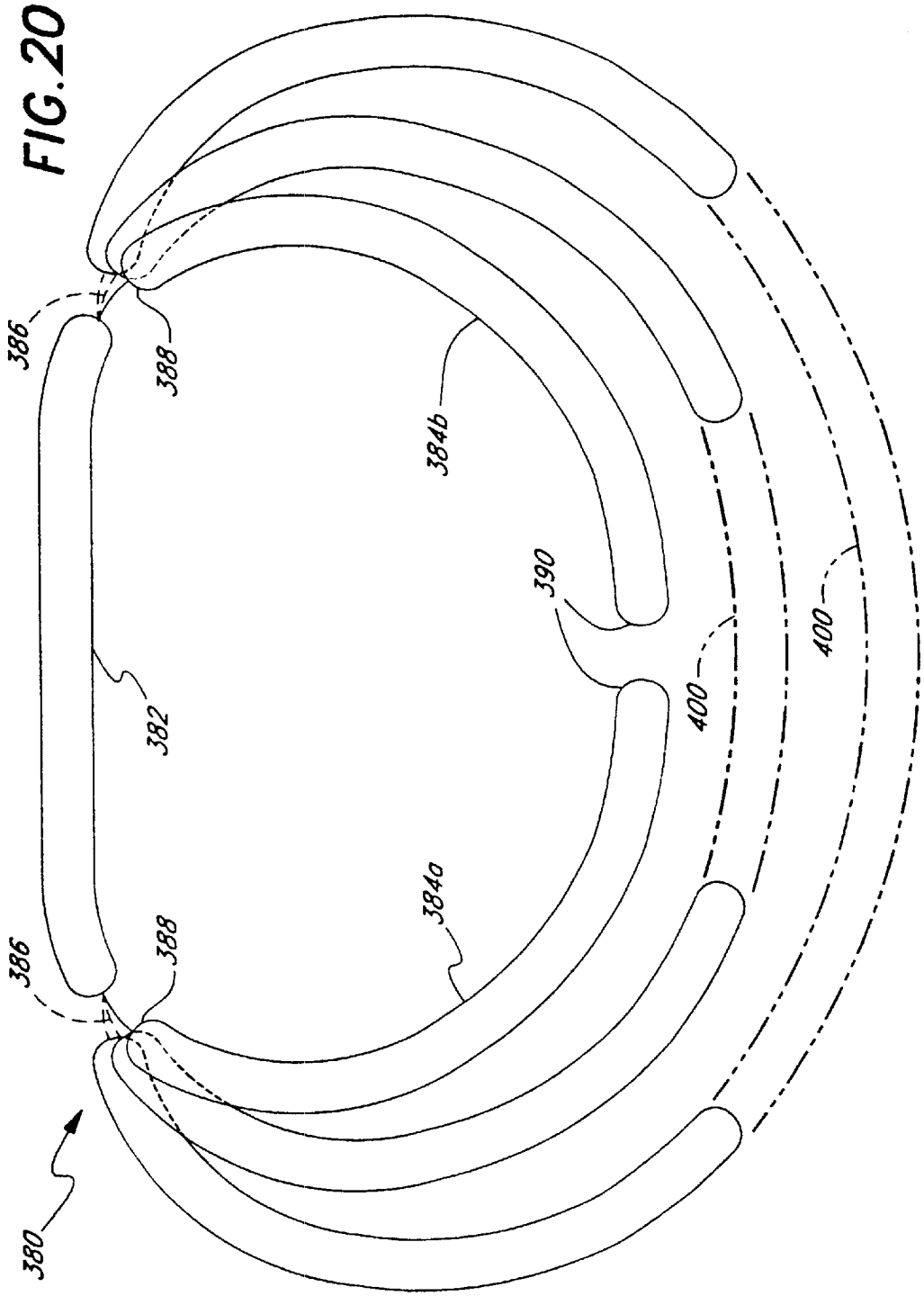
FIG. 20 is a schematic plan view of the three-part expandable annuloplasty ring of FIG. 19 in various stages of expansion upon growth of the annulus.

Expansion of the annuloplasty ring 380 of FIG. 19 is seen in schematic in FIG. 20. As mentioned previously, the generally linear segments 382 remains relatively stable, while the curvilinear segments 384 pivot therefrom and spread apart. The break or discontinuity between the second ends 390 of the curvilinear segments 384 becomes larger as the patient's annulus grows. The dashed lines 400 for the two larger sizes represent imaginary extensions of the curvilinear segments 384 toward one another. It can thus be seen that the overall shape of the annuloplasty ring 380 is substantially maintained even in its expanded configurations.

Continuous, Segmented, Expandable Annuloplasty Rings

In another form of the present invention, the annuloplasty ring comprises segments which are coupled together in a telescoped manner. Unlike the earlier described telescoped embodiments which included various structure to prevent the segments from contracting after expansion, this embodiment allows both expansion and contraction. Because of the foreign body response of the patient, a tubular sheath of tissue forms around annuloplasty rings. By allowing the segments to freely slide circumferentially, the telescoped, segmented ring can expand with the growing tissue sheath.

Figure 21:
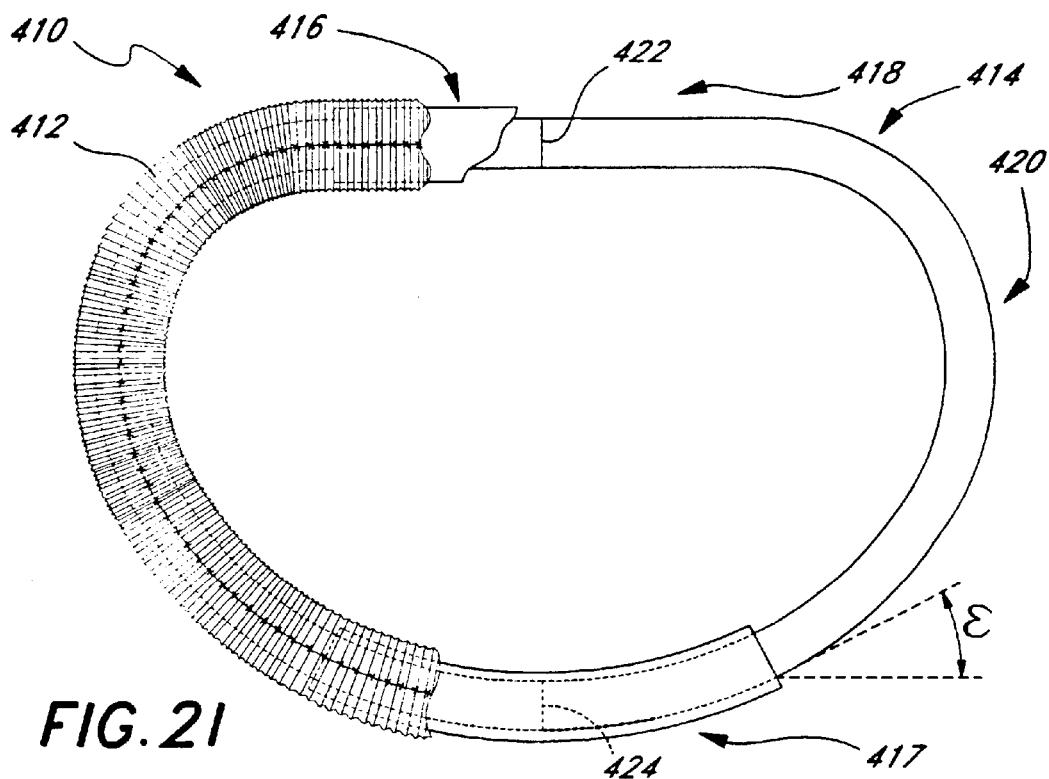
FIG. 21 is a partially cut away plan view of an expandable annuloplasty ring of the present invention utilizing telescoped segments.
Figure 22:
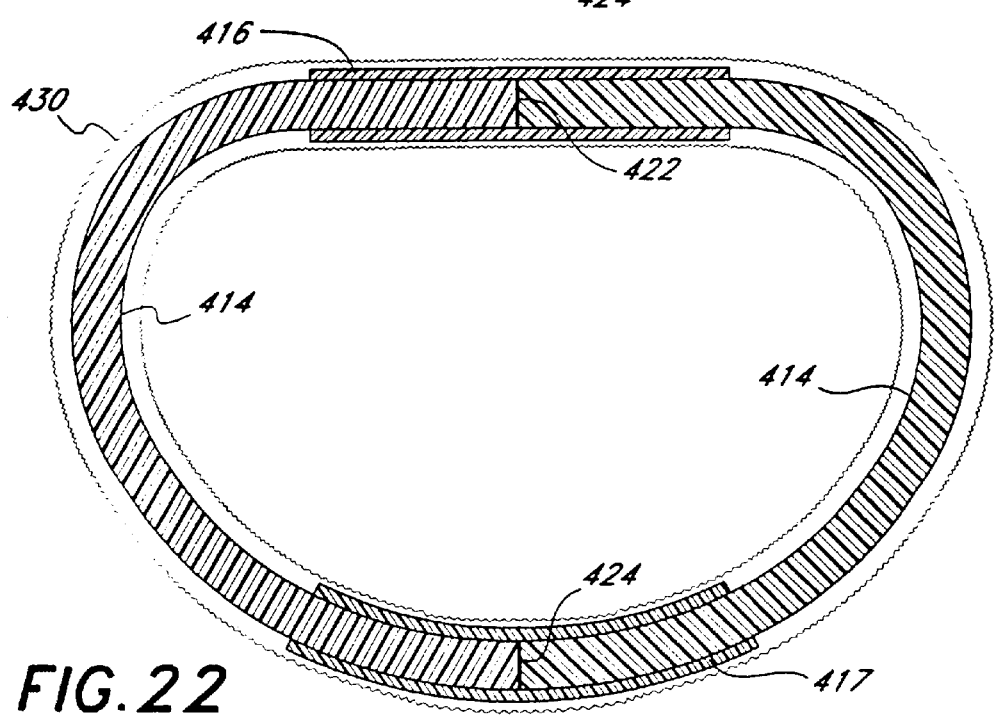
FIG. 22 is a cross-sectional view of the expandable annuloplasty ring of FIG. 21 implanted in tissue.

FIGS. 21 and 22 illustrate a further embodiment of a segmented, expandable annuloplasty ring 410 which maintains a continuous periphery throughout growth of the annulus, and relies on telescoping as opposed to pivoting segments. FIG. 21 illustrates the ring 410 in plan view with a portion of an outer fabric covering 412 cut away to expose the working elements therein. The ring 410 comprises a pair of symmetrical and generally curvilinear segments 414 joined by a pair of tubular sheaths 416 and 417. The segments 414 each comprise a generally linear portion 418 which corresponds to the region of the mitral annulus to which the anterior leaflet attaches, and a curvilinear portion 420 which corresponds to the region of the mitral valve annulus about which the posterior leaflet attaches. The linear portions 418 of the segments 414 meet at a junction 422, while the curvilinear portions 420 meet at a junction 424. Because of the generally D-shape of the ring 410, the junctions 422 and 424 desirably lie along an axis of symmetry of the ring; the segments 414 thus being mirror images of one another.

In the initial, unimplanted, state of the ring 410, the segments 414 are juxtaposed at the junctions 422 and 444. The sheath 416, which is preferably linear, surrounds the linear portions 418 of both segments 414 and the junction 422. Likewise, the sheath 417, which is curvilinear, surrounds the junction 424 and a length of each of the curvilinear portions 420.

The arrangement of the elements of the ring 410 after implantation is seen in cross-section in FIG. 22. After a sufficient time has elapsed, the host organism foreign body response creates a tubular growth of tissue 430 in and around the fabric covering 412, thus encapsulating the elements of the ring 410 within. In a preferred embodiment, the segments 414 and sheaths 416 and 417 are made of a smooth material resistant to tissue ingrowth. For example, the segments 414 may be made of a relatively rigid material or a combination of biocompatible metal and silicone, while the sheaths 416 and 417 are made of pliable silicone or a biocompatible polymer. In this manner, the tubular surrounding tissue 430 will not interfere with subsequent expansion of the ring 410. That is, the ring elements relatively easily slide with respect to and within the surrounding tissue 430. During growth of the annulus, which naturally includes growth of the surrounding tissue 430, the telescoped sections of the ring 410 are able to move apart under influence of the growth forces of the annulus. That is, the segments 414 will move apart which respect to one another within the sheaths 416 and 417. The fabric covering 412 is highly elastic and expands with the growth of the surrounding tissue 430.

Figure 23:
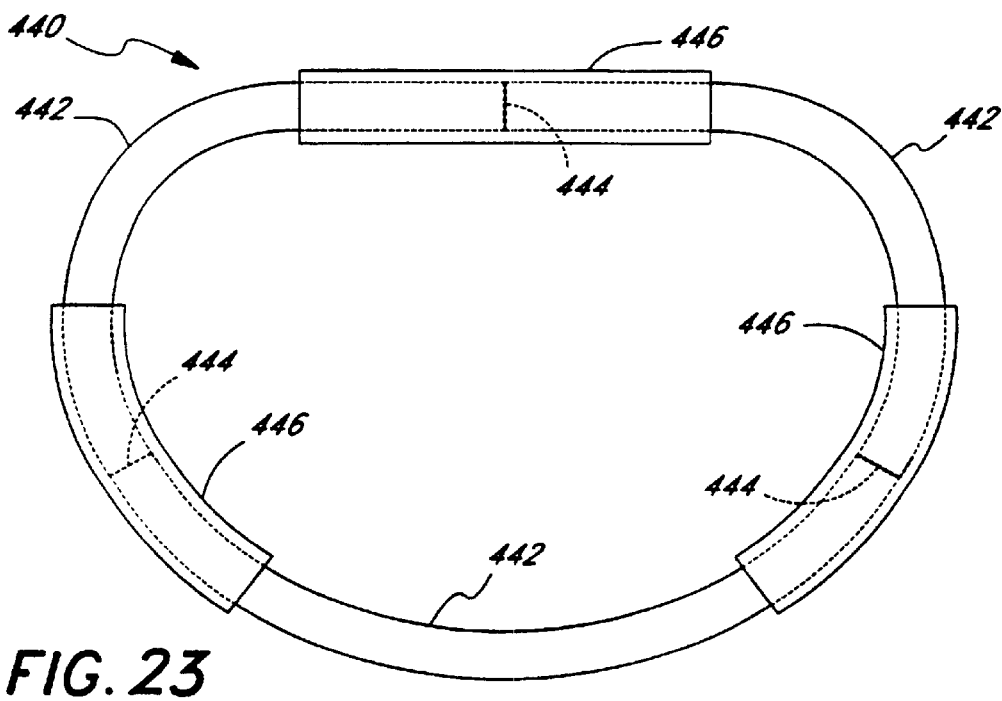
FIG. 23 is a plan view of a further embodiment of an expandable annuloplasty ring having telescoped segments and no fabric covering.

A further embodiment of the telescoped configuration of expandable annuloplasty ring the shown at 440 in FIG. 23. In this version, three segments 442 initially have juxtaposed ends at junctions 444. Sheaths 446 surround the junctions 444 as well as a predetermined length of the respective segments 442. In this embodiment, there is no fabric covering as in FIG. 21, and the annuloplasty ring 440 is implanted by using a technique in which sutures passed through the annulus are looped around the ring, as opposed to being threaded through an associated fabric covering.

Figure 24:
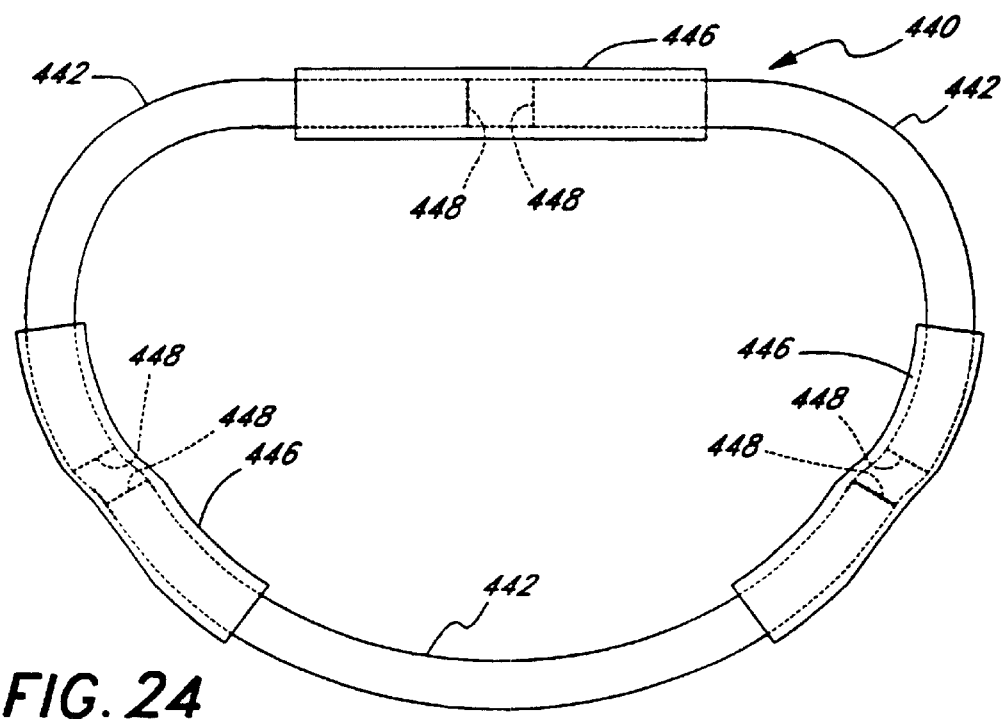
FIG. 24 is a plan view of the expandable annuloplasty ring of FIG. 23 simulating the expansion thereof after a period of time after implantation.

FIG. 24 illustrates the shape of the ring 440 after a period of growth of the host annulus. The segments 442 have been pull apart so that their ends 448 are spaced with respect to one another within the sheaths 446. The sheaths 446 are sufficiently long enough to accommodate substantial growth of the ring 440 without separation of the elements. Again, the shape of the segments 442 and sheaths 446 are such that upon growth of the annulus, the ring 440 maintains its approximate initial shape. The sheaths 446 between curvilinear portions of the segments 442 are deformed to some extent because of the shape and rigidity of the segments, and their separation. Nevertheless, the initial shape (i.e., aspect ratio) is approximately maintained, and the annulus adequately supported despite the slightly changing shape.

It will be appreciated by those skilled in the art that various modification additions and deletions may be made to the above-described embodiments, without departing from the intended spirit and scope of the invention. Accordingly, it is intended that all such modifications, additions and deletions be included within the scope of the following claims.

What is claimed is:

1. An expandable annuloplasty ring for implantation in a developing heart valve annulus of a pediatric human patient, comprising:
   a ring segment defining a periphery of the ring discontinuous at a single location, the ring segment being formed of a non-elastic material which has sufficient pliability to plastically expand in response to forces exerted thereon by the natural growth of he heart valve annulus and sufficient strength to provide adequate support for the heart valve annulus; and
   a radially expandable fabric covering surrounding the ring segment to enable attachment to the annulus.

2. The annuloplasty ring of claim 1, wherein the non-elastic material is a material which exhibits plastic deformation properties and creeps over time.

3. The annuloplasty ring of claim 1, wherein the non-elastic material is a polyacetal.

4. The annuloplasty ring of claim 1, wherein the ring is configured for mitral valve implantation and has a non-circular shape with an anterior side and a posterior side, and wherein the single location is positioned on the anterior side.

5. The annuloplasty ring of claim 4, wherein the ring is generally D-shaped with a straight anterior side.

6. The annuloplasty ring of claim 5, wherein the single location is in the middle of the straight anterior side.

7. The annuloplasty ring of claim 5, wherein the single location is offset from the middle of the straight anterior side.

8. The annuloplasty ring of claim 1, wherein the single location is formed by a break in the ring periphery, so that the ring is open.

9. The annuloplasty ring of claim 1, wherein the single location is formed by a section of the ring that is relatively weaker than the remaining section.

10. The annuloplasty ring of claim 1, wherein the fabric covering has a longitudinal seam.

* * * * *